(12) United States Patent
Charrier et al.

(10) Patent No.: US 8,278,297 B2
(45) Date of Patent: Oct. 2, 2012

(54) PROTEIN KINASE INHIBITORS

(75) Inventors: Jean-Damien Charrier, Abingdon (GB); Steven Durrant, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/977,197

(22) Filed: Dec. 23, 2010

(65) Prior Publication Data

US 2012/0028966 A1  Feb. 2, 2012

Related U.S. Application Data

(63) Continuation of application No. PCT/US2009/003716, filed on Jun. 23, 2009.

(60) Provisional application No. 61/074,754, filed on Jun. 23, 2008.

(51) Int. Cl.
C07D 475/12 (2006.01)
C07D 487/04 (2006.01)
A61K 31/519 (2006.01)

(52) U.S. Cl. ........ 514/220; 514/221; 514/250; 540/502; 540/557; 540/561; 540/562; 540/563; 540/568; 544/257; 544/258

(58) Field of Classification Search .................. 540/502, 540/557, 561, 562, 563, 568; 544/257, 258; 514/220, 221, 250
See application file for complete search history.

(56) References Cited

U.S. PATENT DOCUMENTS

2012/0010197 A1  1/2012  Charrier et al.

FOREIGN PATENT DOCUMENTS

| WO | WO 2005/123736 | 12/2005 |
| WO | WO 2007/095188 | 8/2007 |
| WO | WO 2008/076392 | 6/2008 |
| WO | WO 2009/040556 | 4/2009 |
| WO | WO 2010/008459 | 1/2010 |

OTHER PUBLICATIONS

International Search Report issued for PCT/US2007/025688 Dated Apr. 6, 2008.
International Search Report issued for PCT/US2009/003716 Dated Nov. 20, 2009.
International Search Report issued for PCT/US2009/003723 Dated Nov. 20, 2009.

*Primary Examiner* — Bruck Kifle
(74) *Attorney, Agent, or Firm* — Honigman Miller Schwartz and Cohn LLP; Andrew N. Weber; Jonathan P. O'Brien

(57) ABSTRACT

In one aspect, the invention provides compounds of Formula I

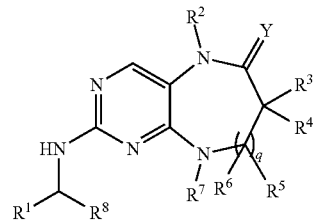

or pharmaceutically acceptable salts thereof. In another aspect, the invention provides methods for treatment of diseases or disorders mediated by a protein kinase, comprising administering a therapeutically effective amount of a compound of this invention.

36 Claims, No Drawings

```
                       SEQUENCE LISTING

<160> NUMBER OF SEQ ID NOS: 4

<210> SEQ ID NO 1
  <211> LENGTH: 19
  <212> TYPE: PRT
  <213> ORGANISM: Artificial Sequence
  <220> FEATURE:
  <223> OTHER INFORMATION: Synthetically Generated Peptide

<400> SEQUENCE: 1

Lys Lys Lys Ile Ser Asp Glu Leu Met Asp Ala Thr Phe Ala Asp Gln
  1               5                   10                  15

Glu Ala Lys

<210> SEQ ID NO 2
  <211> LENGTH: 19
  <212> TYPE: PRT
  <213> ORGANISM: Artificial Sequence
  <220> FEATURE:
  <223> OTHER INFORMATION: Synthetically Generated Peptide

<400> SEQUENCE: 2

Lys Lys Lys Ile Ser Asp Glu Leu Met Asp Ala Thr Phe Ala Asp Gln
  1               5                   10                  15

Glu Ala Lys

<210> SEQ ID NO 3
  <211> LENGTH: 19
  <212> TYPE: PRT
  <213> ORGANISM: Artificial Sequence
  <220> FEATURE:
  <223> OTHER INFORMATION: Synthetically Generated Peptide

<400> SEQUENCE: 3

Lys Lys Lys Ile Ser Asp Glu Leu Met Asp Ala Thr Phe Ala Asp Gln
  1               5                   10                  15

Glu Ala Lys

<210> SEQ ID NO 4
  <211> LENGTH: 11
  <212> TYPE: PRT
  <213> ORGANISM: Artificial Sequence
  <220> FEATURE:
  <223> OTHER INFORMATION: Synthetically Generated Peptide

<400> SEQUENCE: 4

Lys Lys Lys Met Asp Ala Thr Phe Ala Asp Gln
  1               5                   10
```

PROTEIN KINASE INHIBITORS

This application is a continuation of PCT Application No. PCT/US2009/003716, filed on Jun. 23, 2009, which claims priority to U.S. Ser. No. 61/074,754, filed Jun. 23, 2008. The entire contents of these applications are incorporated herein.

BACKGROUND OF THE INVENTION

The search for new therapeutic agents has been greatly aided in recent years by a better understanding of the structure of enzymes and other biomolecules associated with diseases. One important class of enzymes that has been the subject of intensive study is protein kinases.

Protein kinases constitute a large family of structurally related enzymes that are responsible for the control of a variety of signal transduction processes within the cell (see, e.g., G. Hardie et al., *The Protein Kinase Facts Book, I and II*, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases may be categorized into families by the substrates they phosphorylate (e.g., protein-tyrosine, protein-serine/threonine, lipids etc). Sequence motifs have been identified that generally correspond to each of these kinase families (see, e.g., S. K. Hanks et al., *FASEB J.*, 1995, 9, 576-596; Knighton et al., *Science* 1991, 253, 407-414; Hiles et al., *Cell*, 1992, 70, 419-429; Kunz et al., *Cell*, 1993, 73, 585-596; Garcia-Bustos et al., *EMBO J.*, 1994, 13, 2352-2361).

In general, protein kinases mediate intracellular signaling by affecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., shock, heat shock, ultraviolet radiation, bacterial endotoxin, and $H_2O_2$), cytokines (e.g., interleukin-1 (IL-1) and tumor necrosis factor alpha (TNF-a), and growth factors (e.g., granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Many diseases are associated with abnormal cellular responses triggered by protein kinase-mediated events as described above. These diseases include, but are not limited to, cancer, autoimmune diseases, inflammatory diseases, bone diseases, metabolic diseases, neurological and neurodegenerative diseases, cardiovascular diseases, allergies and asthma, Alzheimer's disease and hormone related diseases. Accordingly, there has been a substantial effort in medicinal chemistry to find protein kinase inhibitors that are effective as therapeutic agents.

The Polo-like kinases (PLKs) belong to a family of serine/threonine kinases that are highly conserved across the species, ranging from yeast to man (reviewed in Lowery D M et al., *Oncogene*, 2005, 24, 248-259). The PLKs have multiple roles in cell cycle, including control of entry into and progression through mitosis.

PLK1 is the best characterized of the PLK family members. PLK1 is widely expressed and is most abundant in tissues with a high mitotic index. Protein levels of PLK1 rise and peak in mitosis (see, e.g., R. Hamanaka et al., *J. Biol. Chem.*, 1995, 270, 21086-21091). The reported substrates of PLK1 are all molecules that are known to regulate entry and progression through mitosis, and include CDC25C, cyclin B, p53, APC, BRCA2 and the proteasome. PLK1 is up-regulated in multiple cancer types and the expression levels correlate with severity of disease (see, e.g., Macmillan, J. C. et al., *Ann. Surg. Oncol.*, 2001, 8, 729-740). PLK1 is an oncogene and can transform NIH-3T3 cells (see, e.g., M. R. Smith et al., *Biochem. Biophys. Res. Commun.*, 1997, 234, 397-405). Depletion or inhibition of PLK1 by siRNA, antisense, microinjection of antibodies, or transfection of a dominant negative construct of PLK1 into cells, reduces proliferation and viability of tumor cells in vitro (see, e.g., R. Guan et al., *Cancer Res.*, 2005, 65, 2698-2704; X. Liu et al., *Proc. Nat'l. Acad. Sci. U.S.A.*, 2003, 100, 5789-5794, Y. Fan et al., *World J. Gastroenterol.*, 2005, 11, 4596-4599; H. A. Lane et al., *J. Cell Biol.*, 1996, 135, 1701-1713). Tumor cells that have been depleted of PLK1 have activated spindle checkpoints and defects in spindle formation, chromosome alignment and separation and cytokinesis. Loss in viability has been reported to be the result of an induction of apoptosis. In contrast, normal cells have been reported to maintain viability on depletion of PLK1. In vivo knock down of PLK1 by siRNA or the use of dominant negative constructs leads to growth inhibition or regression of tumors in xenograft models.

PLK2 is mainly expressed during the G1 phase of the cell cycle and is localized to the centrosome in interphase cells. PLK2 knockout mice develop normally, are fertile and have normal survival rates, but are around 20% smaller than wild type mice. Cells from knockout animals progress through the cell cycle more slowly than in normal mice (see, e.g., S. Ma et al., *Mol. Cell. Biol.*, 2003, 23, 6936-6943). Depletion of PLK2 by siRNA or transfection of kinase inactive mutants into cells blocks centriole duplication. Down-regulation of PLK2 also sensitizes tumor cells to taxol and promotes mitotic catastrophe, in part by suppression of the p53 response (see, e.g., T. F. Burns et al., *Mol. Cell. Biol.*, 2003, 23, 5556-5571).

PLK3 is expressed throughout the cell cycle and increases from G1 to mitosis. Expression is up-regulated in highly proliferating ovarian tumors and breast cancer and is associated with a worse prognosis (see, e.g., W. Weichert et al., *Br. J. Cancer*, 2004, 90, 815-821; W. Weichert et al., *Virchows Arch*, 2005, 446, 442-450). In addition to regulation of mitosis, PLK3 is believed to be involved in Golgi fragmentation during the cell cycle and in the DNA-damage response. Inhibition of PLK3 by dominant negative expression is reported to promote p53-independent apoptosis after DNA damage and suppresses colony formation by tumor cells (see, e.g., Z. Li et al., *J. Biol. Chem.*, 2005, 280, 16843-16850).

PLK4 is structurally more diverse from the other PLK family members. Depletion of this kinase causes apoptosis in cancer cells (see, e.g., J. Li et al., *Neoplasia*, 2005, 7, 312-323). PLK4 knockout mice arrest at E7.5 with a high fraction of cells in mitosis and partly segregated chromosomes (see, e.g., J. W. Hudson et al., *Current Biology*, 2001, 11, 441-446).

Molecules of the protein kinase family have been implicated in tumor cell growth, proliferation and survival. Accordingly, there is a great need to develop compounds useful as inhibitors of protein kinases. The evidence implicating the PLK kinases as essential for cell division is strong. Blockade of the cell cycle is a clinically validated approach to inhibiting tumor cell proliferation and viability. It would therefore be desirable to develop compounds that are useful as inhibitors of the PLK family of protein kinases (e.g., PLK1, PLK2, PLK3 and PLK4), that would inhibit proliferation and reduce viability of tumor cells, particularly as there is a strong medical need to develop new treatments for cancer, including treatments that would be administered orally.

SUMMARY OF THE INVENTION

In one aspect, the present invention provides compounds of Formula I shown and described herein, as well as their pharmaceutically acceptable salts.

The compounds of this invention in general are potent inhibitors of protein kinases, such as PLKs (polo-like kinases), e.g., PLK1, PLK2, PLK3, or PLK4. Accordingly, these compounds and their pharmaceutically acceptable salts and compositions are useful for treating or preventing diseases, disorders, or medical conditions implicated or mediated by protein kinases such as PLKs (polo-like kinases), e.g., PLK1, PLK2, PLK3, or PLK4. Examples of such diseases or conditions include cancers, e.g., melanoma, myeloma, leukemia, lymphoma, neuroblastoma, colon cancer, breast cancer, gastric cancer, ovarian cancer, cervical cancer, lung cancer, central nervous system cancer, renal cancer, prostate cancer, bladder cancer, or pancreatic cancer.

The compounds provided by this invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

In one aspect, the invention provides compounds of the Formula I, or a pharmaceutically acceptable salt thereof.

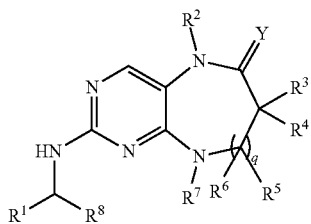

I

In Formula I,
$Y$ is O or $NR^9$;
$R^1$ is aryl or heteroaryl;
$R^2$ is H, alkyl, or cycloalkyl;
each of $R^3$ and $R^4$ is independently H, alkyl, cycloalkyl, aryl, or heteroaryl; or $R^3$ and $R^4$, together with the carbon atom to which they are attached, form a cycloalkyl;
each of $R^5$ and $R^6$ is independently H, alkyl, cycloalkyl, aryl, or heteroaryl;
$R^7$ is H, alkyl, cycloalkyl, aryl, heteroaryl, or heterocyclyl;
$R^8$ is alkyl;
$R^9$ is H or alkyl; or $R^2$ and $R^9$, together with the atoms to which they are attached, optionally form a 5- to 8-membered monocyclic ring containing additional 0 to 2 hetero atoms each independently selected from O, N, and S, wherein said monocyclic ring is optionally substituted with 0 to 4 groups each independently being alkyl, halo, alkoxy, or hydroxy; and
q is 0 or 1.

In some embodiments of compounds of this invention, Y is O.

In some embodiments, $R^2$ is alkyl (e.g., methyl or ethyl).

In some embodiments, $R^3$ and $R^4$ are independently H or alkyl (e.g., methyl or ethyl).

In some embodiments, $R^3$ and $R^4$, together with the carbon atom to which they are attached, form a cycloalkyl (e.g., of $C_{3-5}$), thereby giving rise to a spiro ring system.

In some embodiments, $R^7$ is alkyl or cycloalkyl (for example cyclopentyl).

In some embodiments, each of $R^5$ and $R^6$ is independently H or alkyl (e.g., methyl, ethyl, or propyl).

In some embodiments, $R^8$ is an optionally substituted alkyl (e.g., methyl, ethyl, methoxymethyl, methoxyethyl, hydroxymethyl, or hydroxyethyl).

In some embodiments, when $R^8$ is methyl, the carbon atom to which $R^8$ is attached is generally in the S configuration; whereas when $R^8$ is not methyl (e.g., when it is hydroxymethyl, methoxymethyl, or ethyl), the same carbon atom is generally in the R configuration.

In some embodiments, when $R^8$ is methyl, the carbon atom to which $R^8$ is attached is of the S configuration.

In some embodiments, $R^1$ is optionally substituted phenyl, optionally substituted napthyl, optionally substituted pyridyl, optionally substituted furanyl, or optionally substituted thiazolyl. The optional substituents can range from 1 to 3 in number and can independently be alkyl (e.g., methyl or ethyl), halo (e.g., fluoro or chloro), amino (e.g., amino, dimethylamino, or (dimethylamino)ethyl)(methyl)amino), alkoxy (e.g., methoxy, trifluoromethoxy, or ethoxy), haloalkyl (e.g., trifluoromethyl or chloroethyl), alkylsulfonyl (e.g., tert-butylsulfonyl), nitro, phenyl, 1-piperazinyl, or 4-alkylpiperazin-1-yl.

In some other embodiments, $R^1$ is phenyl optionally substituted with 1 to 3 substituents each independently selected from the group consisting of alkyl, halo, amino, alkoxy, haloalkyl, alkylsulfonyl, nitro, phenyl, 1-piperazinyl, and 4-alkylpiperazin-1-yl.

In some further embodiments, $R^1$ is phenyl, 4-methylphenyl, 4-methoxyphenyl, 3-methoxyphenyl, 2-methoxyphenyl, 3,4-dimethoxyphenyl, 4-(trifluoromethoxy)phenyl, 2-(trifluoromethyl)phenyl, 4-(trifluoromethyl)phenyl, 3-(trifluoromethyl)phenyl, 3,5-bis(trifluoromethyl)phenyl, 4-bromophenyl, 4-chlorophenyl, 4-fluorophenyl, 2-fluorophenyl, 3,5-difluorophenyl, 4-(4-methylpiperazin-1-yl)phenyl, 4-(piperazin-1-yl)phenyl, 4-((2-(dimethylamino)ethyl)(methyl)amino)phenyl, 4-nitrophenyl, 4-(methylsulfonyl)phenyl, biphenyl-4-yl, naphthalenyl, 3-pyridinyl, 2-pyridinyl, 4-pyridinyl, 2-furanyl, 4-thiazolyl, or 2-methylthiazol-4-yl.

Some compounds of this invention can be represented by Formula Ia:

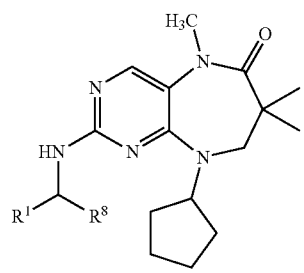

Ia wherein $R^1$ and $R^8$ have been defined herein.

Some specific examples of the compounds of this invention include:

9-cyclopentyl-5,7,7-trimethyl-2-(1-phenylethylamino)-8,9-dihydro-5H-pyrimido[4,5-b][1,4]diazepin-6(7H)-one;
9-cyclopentyl-5,7,7-trimethyl-2-(1-phenylpropylamino)-8,9-dihydro-5H-pyrimido[4,5-b][1,4]diazepin-6(7H)-one;
9-cyclopentyl-2-(2-methoxy-1-phenylethylamino)-5,7,7-trimethyl-8,9-dihydro-5H-pyrimido[4,5-b][1,4]diazepin-6(7H)-one;
9-cyclopentyl-2-(2-hydroxy-1-phenylethylamino)-5,7,7-trimethyl-8,9-dihydro-5H-pyrimido[4,5-b][1,4]diazepin-6(7H)-one;
2-(1-(4-bromophenyl)ethylamino)-9-cyclopentyl-5,7,7-trimethyl-8,9-dihydro-5H-pyrimido[4,5-b][1,4]diazepin-6(7H)-one;
9-cyclopentyl-5,7,7-trimethyl-2-(1-(4-(4-methylpiperazin-1-yl)phenyl)ethylamino)-8,9-dihydro-5H-pyrimido[4,5-b][1,4]diazepin-6(7H)-one
9-cyclopentyl-5,7,7-trimethyl-2-(1-(4-(piperazin-1-yl)phenyl)ethylamino)-8,9-dihydro-5H-pyrimido[4,5-b][1,4]diazepin-6(7H)-one;
9-cyclopentyl-2-(1-(4-((2-(dimethylamino)ethyl)(methyl)amino)phenyl)ethylamino)-5,7,7-trimethyl-8,9-dihydro-5H-pyrimido[4,5-b][1,4]diazepin-6(7H)-one
9-cyclopentyl-5,7,7-trimethyl-2-(1-p-tolylethylamino)-8,9-dihydro-5H-pyrimido[4,5-b][1,4]diazepin-6(7H)-one;
2-(1-(4-chlorophenyl)ethylamino)-9-cyclopentyl-5,7,7-trimethyl-8,9-dihydro-5H-pyrimido[4,5-b][1,4]diazepin-6(7H)-one;
9-cyclopentyl-2-(1-(4-fluorophenyl)ethylamino)-5,7,7-trimethyl-8,9-dihydro-5H-pyrimido[4,5-b][1,4]diazepin-6(7H)-one;
9-cyclopentyl-2-(1-(2-fluorophenyl)ethylamino)-5,7,7-trimethyl-8,9-dihydro-5H-pyrimido[4,5-b][1,4]diazepin-6(7H)-one;
9-cyclopentyl-2-(1-(3,5-difluorophenyl)ethylamino)-5,7,7-trimethyl-8,9-dihydro-5H-pyrimido[4,5-b][1,4]diazepin-6(7H)-one;
9-cyclopentyl-2-(1-(4-methoxyphenyl)ethylamino)-5,7,7-trimethyl-8,9-dihydro-5H-pyrimido[4,5-b][1,4]diazepin-6(7H)-one;
9-cyclopentyl-2-(1-(3-methoxyphenyl)ethylamino)-5,7,7-trimethyl-8,9-dihydro-5H-pyrimido[4,5-b][1,4]diazepin-6(7H)-one;
9-cyclopentyl-2-(1-(2-methoxyphenyl)ethylamino)-5,7,7-trimethyl-8,9-dihydro-5H-pyrimido[4,5-b][1,4]diazepin-6(7H)-one;
9-cyclopentyl-2-(1-(3,4-dimethoxyphenyl)ethylamino)-5,7,7-trimethyl-8,9-dihydro-5H-pyrimido[4,5-b][1,4]diazepin-6(7H)-one;
9-cyclopentyl-5,7,7-trimethyl-2-(1-(4-(trifluoromethoxy)phenyl)ethylamino)-8,9-dihydro-5H-pyrimido[4,5-b][1,4]diazepin-6(7H)-one;
9-cyclopentyl-5,7,7-trimethyl-2-(1-(4-(trifluoromethyl)phenyl)ethylamino)-8,9-dihydro-5H-pyrimido[4,5-b][1,4]diazepin-6(7H)-one;
9-cyclopentyl-5,7,7-trimethyl-2-(1-(3-(trifluoromethyl)phenyl)ethylamino)-8,9-dihydro-5H-pyrimido[4,5-b][1,4]diazepin-6(7H)-one;
2-(1-(3,5-bis(trifluoromethyl)phenyl)ethylamino)-9-cyclopentyl-5,7,7-trimethyl-8,9-dihydro-5H-pyrimido[4,5-b][1,4]diazepin-6(7H)-one;
9-cyclopentyl-5,7,7-trimethyl-2-(1-(2-(trifluoromethyl)phenyl)ethylamino)-8,9-dihydro-5H-pyrimido[4,5-b][1,4]diazepin-6(7H)-one;
9-cyclopentyl-5,7,7-trimethyl-2-(1-(4-nitrophenyl)ethylamino)-8,9-dihydro-5H-pyrimido[4,5-b][1,4]diazepin-6(7H)-one;
9-cyclopentyl-5,7,7-trimethyl-2-(1-(4-(methylsulfonyl)phenyl)ethylamino)-8,9-dihydro-5H-pyrimido[4,5-b][1,4]diazepin-6(7H)-one;
2-(1-(biphenyl-4-yl)ethylamino)-9-cyclopentyl-5,7,7-trimethyl-8,9-dihydro-5H-pyrimido[4,5-b][1,4]diazepin-6(7H)-one;
9-cyclopentyl-5,7,7-trimethyl-2-(1-(naphthalen-1-yl)ethylamino)-8,9-dihydro-5H-pyrimido[4,5-b][1,4]diazepin-6(7H)-one;
9-cyclopentyl-5,7,7-trimethyl-2-(1-(pyridin-3-yl)ethylamino)-8,9-dihydro-5H-pyrimido[4,5-b][1,4]diazepin-6(7H)-one;
9-cyclopentyl-5,7,7-trimethyl-2-(1-(pyridin-2-yl)ethylamino)-8,9-dihydro-5H-pyrimido[4,5-b][1,4]diazepin-6(7H)-one
9-cyclopentyl-5,7,7-trimethyl-2-(1-(pyridin-4-yl)ethylamino)-8,9-dihydro-5H-pyrimido[4,5-b][1,4]diazepin-6(7H)-one;
9-cyclopentyl-2-(1-(furan-2-yl)ethylamino)-5,7,7-trimethyl-8,9-dihydro-5H-pyrimido[4,5-b][1,4]diazepin-6(7H)-one; or
9-cyclopentyl-5,7,7-trimethyl-2-(1-(2-methylthiazol-4-yl)ethylamino)-8,9-dihydro-5H-pyrimido[4,5-b][1,4]diazepin-6(7H)-one.

In some embodiments of the compounds of this invention, q is 0.

In some other embodiments, each of $R^3$ and $R^4$ is independently H, or alkyl (e.g., methyl or ethyl).

In some further embodiments, $R^3$ is ethyl and $R^4$ is H.

In some embodiments, when $R^3$ is ethyl and $R^4$ is H, the carbon atom to which $R^3$ and $R^4$ are attached is of the R configuration.

In some embodiments, $R^1$ is an optionally substituted aryl or optionally substituted heteroaryl. The optional substituents can range from 1 to 3 in number and can each independently be alkyl, halo, amino, alkoxy, haloalkyl, alkylsulfonyl, nitro, phenyl, 1-piperazinyl, or 4-methylpiperazin-1-yl.

In some further embodiments, $R^1$ is phenyl which is optionally substituted with 1 to 3 substituents each independently being alkyl (e.g., methyl or ethyl), halo (e.g., fluoro or chloro), amino (e.g., amino, dimethylamino, or (dimethylamino)ethyl(methylamino)), alkoxy (e.g., methoxy, trifluoromethoxy, or ethoxy), haloalkyl (e.g., trifluoromethyl or chloroethyl), alkylsulfonyl (e.g., tert-butylsulfonyl), nitro, phenyl, 1-piperazinyl, or 4-alkylpiperazin-1-yl.

In some embodiments, $R^8$ is optionally substituted alkyl (e.g., methyl, ethyl, methoxymethyl, methoxyethyl, hydroxymethyl, or hydroxyethyl), or optionally substituted cycloalkyl (e.g., cyclopropyl or cyclobutyl).

Some compounds of this invention can be represented by Formula Ib:

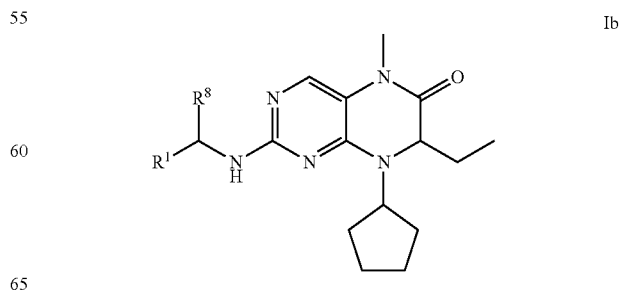

wherein $R^1$ and $R^8$ are defined herein.

A further specific example of the compounds of this invention is:

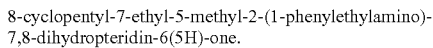

8-cyclopentyl-7-ethyl-5-methyl-2-(1-phenylethylamino)-7,8-dihydropteridin-6(5H)-one.

In some other embodiments of the compounds of this invention, Y is $NR^9$.

In some further embodiments, $R^2$ and $R^9$, together with the atoms to which they are attached, form a 5- to 8-membered monocyclic ring containing additional 0 to 2 hetero atoms each independently being O, N, or S, and the monocyclic ring is optionally substituted with 0 to 4 substituents each independently being halo or alkyl (e.g., methyl, chloromethyl, or ethyl).

In some embodiments, Y is $NR^9$ and q is 0.

In some embodiments, each of $R^3$ and $R^4$ is independently H or alkyl (e.g., methyl or ethyl).

In some further embodiments, $R^3$ is ethyl and $R^4$ is H.

In some embodiments, $R^7$ is cycloalkyl (e.g., cyclopentyl) or aryl (e.g., phenyl).

In some embodiments, $R^1$ is optionally substituted aryl (e.g., p-bromophenyl) or optionally substituted heteroaryl (e.g., 4-methypiperazin-1-yl).

In some embodiments, $R^8$ is alkyl (e.g., methyl, ethyl, methoxymethyl, methoxyethyl, hydroxymethyl, or hydroxyethyl).

Some compounds of this invention can be represented by Formula Ic:

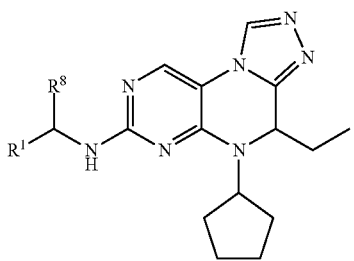

Ic

Further examples of the compounds of this invention include:

5-cyclopentyl-4-ethyl-N-(1-phenylethyl)-4,5-dihydro-[1,2,4]triazolo[4,3-f]pteridin-7-amine;
N-(1-(4-bromophenyl)ethyl)-5-cyclopentyl-4-ethyl-4,5-dihydro-[1,2,4]triazolo[4,3-f]pteridin-7-amine;
5-cyclopentyl-4-ethyl-N-(1-(4-(4-methylpiperazin-1-yl)phenyl)ethyl)-4,5-dihydro-[1,2,4]triazolo[4,3-f]pteridin-7-amine; or
5-cyclopentyl-4-ethyl-N-(1-(4-(piperazin-1-yl)phenyl)ethyl)-4,5-dihydro-[1,2,4]triazolo[4,3-f]pteridin-7-amine
4-ethyl-5-phenyl-N-(1-phenylethyl)-4,5-dihydro-[1,2,4]triazolo[4,3-f]pteridin-7-amine Additional examples of the compounds of this invention include the following:
(S)-9-cyclopentyl-5,7,7-trimethyl-2-(1-phenylethylamino)-8,9-dihydro-5H-pyrimido[4,5-b][1,4]diazepin-6(7H)-one;
(S)-9-cyclopentyl-5,7,7-trimethyl-2-(1-phenylpropylamino)-8,9-dihydro-5H-pyrimido[4,5-b][1,4]diazepin-6(7H)-one;
(R)-9-cyclopentyl-2-(2-methoxy-1-phenylethylamino)-5,7,7-trimethyl-8,9-dihydro-5H-pyrimido[4,5-b][1,4]diazepin-6(7H)-one;
(R)-9-cyclopentyl-2-(2-hydroxy-1-phenylethylamino)-5,7,7-trimethyl-8,9-dihydro-5H-pyrimido[4,5-b][1,4]diazepin-6(7H)-one;
(S)-2-(1-(4-bromophenyl)ethylamino)-9-cyclopentyl-5,7,7-trimethyl-8,9-dihydro-5H-pyrimido[4,5-b][1,4]diazepin-6(7H)-one;
(S)-9-cyclopentyl-5,7,7-trimethyl-2-(1-(4-(4-methylpiperazin-1-yl)phenyl)ethylamino)-8,9-dihydro-5H-pyrimido[4,5-b][1,4]diazepin-6(7H)-one;
(S)-9-cyclopentyl-5,7,7-trimethyl-2-(1-p-tolylethylamino)-8,9-dihydro-5H-pyrimido[4,5-b][1,4]diazepin-6(7H)-one;
(S)-2-(1-(4-chlorophenyl)ethylamino)-9-cyclopentyl-5,7,7-trimethyl-8,9-dihydro-5H-pyrimido[4,5-b][1,4]diazepin-6(7H)-one;
(S)-9-cyclopentyl-2-(1-(4-fluorophenyl)ethylamino)-5,7,7-trimethyl-8,9-dihydro-5H-pyrimido[4,5-b][1,4]diazepin-6(7H)-one;
(S)-9-cyclopentyl-2-(1-(4-methoxyphenyl)ethylamino)-5,7,7-trimethyl-8,9-dihydro-5H-pyrimido[4,5-b][1,4]diazepin-6(7H)-one;
(S)-9-cyclopentyl-2-(1-(3-methoxyphenyl)ethylamino)-5,7,7-trimethyl-8,9-dihydro-5H-pyrimido[4,5-b][1,4]diazepin-6(7H)-one;
(S)-9-cyclopentyl-2-(1-(2-methoxyphenyl)ethylamino)-5,7,7-trimethyl-8,9-dihydro-5H-pyrimido[4,5-b][1,4]diazepin-6(7H)-one;
(S)-9-cyclopentyl-5,7,7-trimethyl-2-(1-(2-(trifluoromethyl)phenyl)ethylamino)-8,9-dihydro-5H-pyrimido[4,5-b][1,4]diazepin-6(7H)-one;
(S)-9-cyclopentyl-5,7,7-trimethyl-2-(1-(4-nitrophenyl)ethylamino)-8,9-dihydro-5H-pyrimido[4,5-b][1,4]diazepin-6(7H)-one;
(RS)-9-cyclopentyl-5,7,7-trimethyl-2-(1-(4-(methylsulfonyl)phenyl)ethylamino)-8,9-dihydro-5H-pyrimido[4,5-b][1,4]diazepin-6(7H)-one;
(RS)-2-(1-(biphenyl-4-yl)ethylamino)-9-cyclopentyl-5,7,7-trimethyl-8,9-dihydro-5H-pyrimido[4,5-b][1,4]diazepin-6(7H)-one;
(RS)-9-cyclopentyl-5,7,7-trimethyl-2-(1-(naphthalen-1-yl)ethylamino)-8,9-dihydro-5H-pyrimido[4,5-b][1,4]diazepin-6(7H)-one;
(RS)-9-cyclopentyl-5,7,7-trimethyl-2-(1-(pyridin-3-yl)ethylamino)-8,9-dihydro-5H-pyrimido[4,5-b][1,4]diazepin-6(7H)-one;
(RS)-9-cyclopentyl-5,7,7-trimethyl-2-(1-(pyridin-4-yl)ethylamino)-8,9-dihydro-5H-pyrimido[4,5-b][1,4]diazepin-6(7H)-one;
(RS)-9-cyclopentyl-2-(1-(furan-2-yl)ethylamino)-5,7,7-trimethyl-8,9-dihydro-5H-pyrimido[4,5-b][1,4]diazepin-6(7H)-one;
(RS)-9-cyclopentyl-2-(1-(3,4-dimethoxyphenyl)ethylamino)-5,7,7-trimethyl-8,9-dihydro-5H-pyrimido[4,5-b][1,4]diazepin-6(7H)-one;
(RS)-9-cyclopentyl-5,7,7-trimethyl-2-(1-(4-(trifluoromethoxy)phenyl)ethylamino)-8,9-dihydro-5H-pyrimido[4,5-b][1,4]diazepin-6(7H)-one;
(R)—N—((S)-1-(4-bromophenyl)ethyl)-5-cyclopentyl-4-ethyl-4,5-dihydro-[1,2,4]triazolo[4,3-f]pteridin-7-amine;
(R)-5-cyclopentyl-4-ethyl-N—((S)-1-phenylethyl)-4,5-dihydro-[1,2,4]triazolo[4,3-f]pteridin-7-amine;
(R)-8-cyclopentyl-7-ethyl-5-methyl-2-((S)-1-phenylethylamino)-7,8-dihydropteridin-6(5H)-one;

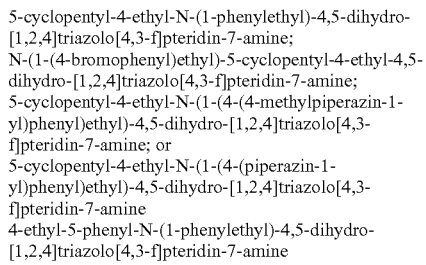

(S)-9-cyclopentyl-2-(1-(4-((2-(dimethylamino)ethyl)(methyl)amino)phenyl)ethylamino)-5,7,7-trimethyl-8,9-dihydro-5H-pyrimido[4,5-b][1,4]diazepin-6(7H)-one;
(R,S)-9-cyclopentyl-5,7,7-trimethyl-2-(1-(2-methylthiazol-4-yl)ethylamino)-8,9-dihydro-5H-pyrimido[4,5-b][1,4]diazepin-6(7H)-one;
(S)-9-cyclopentyl-5,7,7-trimethyl-2-(1-(3-(trifluoromethyl)phenyl)ethylamino)-8,9-dihydro-5H-pyrimido[4,5-b][1,4]diazepin-6(7H)-one;
(R,S)-9-cyclopentyl-2-(1-(2-fluorophenyl)ethylamino)-5,7,7-trimethyl-8,9-dihydro-5H-pyrimido[4,5-b][1,4]diazepin-6(7H)-one;
(R,S)-9-cyclopentyl-2-(1-(3,5-difluorophenyl)ethylamino)-5,7,7-trimethyl-8,9-dihydro-5H-pyrimido[4,5-b][1,4]diazepin-6(7H)-one;
(S)-9-cyclopentyl-5,7,7-trimethyl-2-(1-(4-(trifluoromethyl)phenyl)ethylamino)-8,9-dihydro-5H-pyrimido[4,5-b][1,4]diazepin-6(7H)-one;
(S)-2-(1-(3,5-bis(trifluoromethyl)phenyl)ethylamino)-9-cyclopentyl-5,7,7-trimethyl-8,9-dihydro-5H-pyrimido[4,5-b][1,4]diazepin-6(7H)-one;
(R)-4-ethyl-5-phenyl-N—((S)-1-phenylethyl)-4,5-dihydro-[1,2,4]triazolo[4,3-f]pteridin-7-amine;
(R)—N—((S)-1-(4-bromophenyl)ethyl)-5-cyclopentyl-4-ethyl-4,5-dihydro-[1,2,4]triazolo[4,3-f]pteridin-7-amine;
(R)-5-cyclopentyl-4-ethyl-N—((S)-1-(4-(4-methylpiperazin-1-yl)phenyl)ethyl)-4,5-dihydro-[1,2,4]triazolo[4,3-f]pteridin-7-amine; and
(R)-5-cyclopentyl-4-ethyl-N—((S)-1-(4-(piperazin-1-yl)phenyl)ethyl)-4,5-dihydro-[1,2,4]triazolo[4,3-f]pteridin-7-amine.

Unless otherwise stated, structures depicted or described herein are also meant to include all isomeric (e.g., enantiomeric, diastereomeric, geometric, or conformational) forms of the structures, e.g., the R and S configurations for each asymmetric center, (Z) and (E) double bond isomers, and (Z) and (E) conformational isomers. Accordingly, single stereochemical isomers as well as enantiomeric, diastereomeric, geometric, or conformational mixtures of the present compounds are within the scope of the invention. Likewise, unless otherwise stated, all tautomeric forms of the compounds of the invention are within the scope of the invention.

As used herein, the term "S configuration" or "R configuration" is consistent with the commonly acceptable CIP system, as devised by R. S. Cahn, C. K. Ingold, and V. Prelog. For a detailed description of the system, see, e.g., IUPAC Rules for the Nomenclature of Organic Chemistry, Section E, Stereochemistry (Recommendations 1974), in *Pure & Appl. Chem.*, Vol. 45, pp. 11-30, Pergamon Press, 1976 (Great Britain), the content of which is incorporated herein by reference in its entirety.

Unless otherwise stated, the compounds of this invention include their pharmaceutically acceptable salts, prodrugs, or derivatives.

As used herein, the term a "pharmaceutically acceptable salt" of a compound of this invention refers to a salt which, within the scope of sound medical judgment, is suitable for use in contact with the tissues of humans and lower animals without undue toxicity, irritation, allergic response and the like, and are commensurate with a reasonable benefit/risk ratio.

Pharmaceutically acceptable salts are well known in the art. For example, S. M. Berge et al. describe pharmaceutically acceptable salts in detail in *J. Pharm. Sci.*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared, e.g., by first reacting the purified compound in its free-based form with a suitable organic or inorganic acid and then isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Base addition salts can be prepared, e.g., by first reacting the purified compound in its acid form with a suitable organic or inorganic base and then isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate, or aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, but are not limited to, esters, amino acid esters, phosphate esters, metal salts, and sulfonate esters.

The compounds of this invention in general exhibit unexpected high activities in inhibiting protein kinases, e.g., PLKs (such as PLK1), and thus can be used for treatment of diseases, disorders, or medical conditions mediated by these protein kinases.

Accordingly, the present invention also provides pharmaceutical compositions each containing one or more of the compounds described or specifically named above and a pharmaceutically acceptable carrier, adjuvant, or vehicle.

In certain embodiments, these compositions optionally further comprise one or more additional therapeutic agents. For instance, chemotherapeutic agents or other anti-proliferative agents may be combined with the compounds of this invention to treat proliferative diseases and cancer.

Examples of known chemotherapeutic agents include, but are not limited to, Gleevec™, adriamycin, dexamethasone, vincristine, cyclophosphamide, fluorouracil, topotecan, taxol, interferons, and platinum derivatives.

Other examples of agents with which the compounds of this invention may also be combined include, but are not limited to, agents for treating Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and antiviral agents; agents for treating blood disorders such as corticosteroids, anti-leukemic agents, and growth factors; and agents for treating immunodeficiency disorders such as gamma globulin.

As described herein, a "pharmaceutically acceptable carrier, adjuvant, or vehicle," as used herein, refers to any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds of this invention or pharmaceutical salts thereof may be formulated into pharmaceutically acceptable compositions for administration to animals or humans.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect. In a preferred embodiment, compounds of this invention are administered orally.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it may be desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried corn-starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of protein kinase inhibitor that may be combined with the carrier materials to produce a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

As mentioned above, the compounds of this invention in general have unexpectedly high inhibitory effect on protein kinases such as PLKs (e.g., PLK1, PLK2, PLK3, or PLK4), which are often involved in proliferative disorders, neurodegenerative disorders, autoimmune disorders, inflammatory disorders, and immunologically mediated disorders.

Additionally, the invention provides a method for inhibiting a protein kinase (such as PLK (e.g., PLK1)) by contacting the protein kinase with one or more compounds of this invention or a pharmaceutically acceptable composition of this invention. Examples of protein kinase that can be so inhibited include PLKs (e.g., PLK1 or PLK2).

In another aspect, the present invention provides a method for inhibiting a protein kinase in a patient, which includes administering to the patient in need of such treatment a pharmaceutically effective amount of one or more compounds of this invention (described above), or a pharmaceutical composition of this invention. The protein kinase in the patient can be a PLK (e.g., PLK1 or PLK2).

The invention also provides methods for treating or preventing a protein kinase-mediated condition (in some embodiments, a PLK-mediated condition) comprising the step of administering to a patient one of the above-described pharmaceutical compositions. The term "patient", as used herein, means an animal, preferably a human.

In some embodiments, the methods are used to treat or prevent a disease, disorder, or medical condition which is selected from a proliferative disorder, a neurodegenerative disorder, an autoimmune disorder, an inflammatory disorder, or an immunologically-mediated disorder.

Examples of proliferative disorders include cancers, which can be, e.g., cancers of the breast, colon, prostate, skin, pancreas, brain, genitourinary tract, lymphatic system, stomach, larynx and lung, including lung adenocarcinoma and small cell lung cancer; stroke, diabetes, myeloma, hepatomegaly, cardiomegaly, Alzheimer's disease, cystic fibrosis, and viral disease, or any specific disease described above.

In some embodiments, the methods of this invention can further include administering to the patient a chemotherapeutic agent, an anti-proliferative agent, an anti-inflammatory agent, an immunomodulatory agent, an immunosuppressive agent, a neurotrophic factor, an agent for treating cardiovascular disease, an agent for treating destructive bone disorder, an agent for treating liver disease, an anti-viral agent, an agent for treating blood disorder, an agent for treating diabetes, or an agent for treating immunodeficiency disorder, in addition to one or more compounds or pharmaceutical composition of this invention.

In yet another aspect, the present invention provides a method for treating cancer (such as melanoma, myeloma, leukemia, lymphoma, neuroblastoma, colon cancer, breast cancer, gastric cancer, ovarian cancer, cervical cancer, lung cancer, central nervous system cancer, renal cancer, prostate cancer, bladder cancer, or pancreatic cancer) in a patient, which includes administering to the patient in need thereof a pharmaceutically effective amount of one or more compounds of this invention or a pharmaceutical composition of this invention.

Also provided by the method of invention is a method for disrupting mitosis of cancer cells by inhibiting PLKs, which includes using one or more compounds of this invention described by any of the above embodiments.

One aspect of this invention provides compounds that are useful for the treatment of diseases, disorders, and conditions characterized by excessive or abonormal cell proliferation, by administering to a subject in need thereof an effective amount of a compound of this invention, or a pharmaceutically acceptable composition comprising a compound of this invention. Such diseases include, but are not limited to, proliferative or hyperproliferative diseases (e.g., cancer), and neurodegenerative diseases (e.g., Alzheimer's disease).

As used herein, an "effective amount" of the compound or pharmaceutically acceptable composition is that amount effective in order to treat a target disease. The compound and composition, according to the method of the present invention, may be administered using any amount and any route of administration effective for treating or lessening the severity of the target disease.

The exact amount of compound required for treatment will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient," as used herein, means an animal, preferably a mammal, and most preferably a human.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

In some embodiments, the compounds of this invention are useful for treating cancer (such as colorectal, thyroid, breast, and lung cancer) and myeloproliferative disorders (such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease).

As used herein, the term "cancer" includes, but is not limited to, the following cancers: breast; ovary; cervix; prostate; testis, genitourinary tract; esophagus; larynx, glioblastoma; neuroblastoma; stomach; skin, keratoacanthoma; lung, epidermoid carcinoma, large cell carcinoma, small cell carcinoma, lung adenocarcinoma; bone; colon; colorectal; adenoma; pancreas, adenocarcinoma; thyroid, follicular carcinoma, undifferentiated carcinoma, papillary carcinoma; seminoma; melanoma; sarcoma; bladder carcinoma; liver carcinoma and biliary passages; kidney carcinoma; myeloid disorders; lymphoid disorders, Hodgkin's, hairy cells; buccal cavity and pharynx (oral), lip, tongue, mouth, pharynx; small intestine; colon-rectum, large intestine, rectum; brain and central nervous system; chronic myeloid leukemia (CML); leukaemia; myeloma; lymphoma; gastric; renal; head and neck; oropharangeal; non-small cell lung cancer (NSCLC); endometrial; hepatocarcinoma; Non-Hodgkins lymphoma; and pulmonary.

For the avoidance of doubt, the term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. As used herein, the term "cancerous cell" includes a cell afflicted by any one of the above-identified conditions.

In some embodiments, the compounds of this invention are useful for treating hematopoietic disorders. Examples of such hematopoietic disorders include, but are not limited to, acute-myelogenous leukemia (AML), chronic-myelogenous leukemia (CML), acute-promyelocytic leukemia (APL), and acute lymphocytic leukemia (ALL).

In some embodiments, the disease that can be treated by the methods of this invention is a protein kinase-mediated disease, disorder, or medical condition. Examples of the protein kinase that mediates such a disease, disorder, or medical condition include, but are not limited to, PLKs (e.g., PLK1, PLK2, PLK3, and PLK4).

The term "protein kinase-mediated condition," as used herein, means any disease, disorder, or other deleterious condition in which a protein kinase plays a role. Such conditions include, but are not limited to, autoimmune diseases, inflammatory diseases, proliferative and hyperproliferative diseases, immunologically-mediated diseases, bone diseases, metabolic diseases, neurological and neurodegenerative diseases, cardiovascular diseases, hormone related diseases, allergies, asthma, and Alzheimer's disease.

The term "PLK-mediated condition", as used herein, means any disease or other deleterious condition in which PLK plays a role. Examples of such a disease or condition include, but are not limited to, proliferative or hyperproliferative diseases, or neurodegenerative diseases.

The compounds of this invention include those described herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, *Handbook of Chemistry and Physics*, 75$^{th}$ Ed. Additionally, general principles of organic chemistry are described in *Organic Chemistry*, Thomas Sorrell, University Science Books, Sausalito (1999), and *March's Advanced Organic Chemistry*, 5$^{th}$ Ed. (Eds.: M. B. Smith and J. March), John Wiley & Sons, New York (2001), the entire contents of which are incorporated herein by reference.

As described herein, a specified number range includes any integer therein, as well as the upper and lower limits thereof. For example, a group having 1-4 (i.e., from 1 to 4) atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, recovery, purification, and use for one or more of the purposes disclosed herein. In some embodiments, a stable compound or chemically feasible compound is one that is not substantially altered when kept at a temperature of 40° C. or lower, in the absence of moisture or other chemically reactive conditions, for at least a week.

The term "aliphatic" or "aliphatic group," as used herein, means a straight-chain (i.e., unbranched), branched, or cyclic substituted or unsubstituted hydrocarbon chain that is completely saturated or that contains one or more units of unsaturation that has a single point of attachment to the rest of the molecule. Unless otherwise specified, aliphatic groups contain 1-20 (e.g., 1-10, 1-8, 1-6, or 1-4) aliphatic carbon atoms. It should be understood that if the aliphatic is alkenyl or alkynyl, then it has at least 2 carbon atoms.

Suitable aliphatic groups encompass linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

As used herein, an "alkyl" group refers to a saturated aliphatic hydrocarbon group containing 1 to 12 (e.g., 1 to 10, 1 to 8, 1 to 6, or 1 to 4) carbon atoms. An alkyl group can be straight or branched. Examples of alkyl groups include, but are not limited to, methyl, ethyl, propyl, isopropyl, butyl, isobutyl, sec-butyl, tert-butyl, n-pentyl, n-heptyl, or 2-ethylhexyl. An alkyl group can be substituted (i.e., optionally substituted) with one or more substituents such as halo, phospho, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, or heterocycloaliphaticamino), sulfonyl (e.g., aliphatic-SO2-), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroarylalkoxy, alkoxycarbonyl, alkylcarbonyloxy, or hydroxy. Without limitation, some examples of substituted alkyls include carboxyalkyl (such as HOOC-alkyl, alkoxycarbonylalkyl, and alkylcarbonyloxyalkyl), cyanoalkyl, hydroxyalkyl, alkoxyalkyl, acylalkyl, aralkyl, (alkoxyaryl)alkyl, (sulfonylamino)alkyl (such as (alkyl-SO2-amino)alkyl), aminoalkyl, amidoalkyl, (cycloaliphatic)alkyl, or haloalkyl.

As used herein, an "alkenyl" group refers to an aliphatic carbon group that contains 2 to 12 (e.g., 2 to 8, 2 to 6, or 2 to 4) carbon atoms and at least one double bond. Like an alkyl group, an alkenyl group can be straight or branched. Examples of an alkenyl group include, but are not limited to, allyl, isoprenyl, 2-butenyl, and 2-hexenyl. An alkenyl group can be optionally substituted with one or more substituents such as halo, phospho, cycloaliphatic (e.g., cycloalkyl or cycloalkenyl), heterocycloaliphatic (e.g., heterocycloalkyl or heterocycloalkenyl), aryl, heteroaryl, alkoxy, aroyl, heteroaroyl, acyl (e.g., (aliphatic)carbonyl, (cycloaliphatic)carbonyl, or (heterocycloaliphatic)carbonyl), nitro, cyano, amido (e.g., (cycloalkylalkyl)carbonylamino, arylcarbonylamino, aralkylcarbonylamino, (heterocycloalkyl)carbonylamino, (heterocycloalkylalkyl)carbonylamino, heteroarylcarbonylamino, heteroaralkylcarbonylamino alkylaminocarbonyl, cycloalkylaminocarbonyl, heterocycloalkylaminocarbonyl, arylaminocarbonyl, or heteroarylaminocarbonyl), amino (e.g., aliphaticamino, cycloaliphaticamino, heterocycloaliphaticamino, or aliphaticsulfonylamino), sulfonyl (e.g., alkyl-SO2-, cycloaliphatic-SO2-, or aryl-SO2-), sulfinyl, sulfanyl, sulfoxy, urea, thiourea, sulfamoyl, sulfamide, oxo, carboxy, carbamoyl, cycloaliphaticoxy, heterocycloaliphaticoxy, aryloxy, heteroaryloxy, aralkyloxy, heteroaralkoxy, alkoxycarbonyl, alkylcarbonyloxy, or hydroxy. Without limitation, some examples of substituted alkenyls include cyanoalkenyl, alkoxyalkenyl, acylalkenyl, hydroxyalkenyl, aralkenyl, (alkoxyaryl)alkenyl, (sulfonylamino)alkenyl (such as (alkyl-SO2-amino)alkenyl), aminoalkenyl, amidoalkenyl, (cycloaliphatic)alkenyl, or haloalkenyl.

As used herein, an "alkynyl" group refers to an aliphatic carbon group that contains 2 to 12 (e.g., 2 to 8, 2 to 6, or 2 to 4) carbon atoms and has at least one triple bond. An alkynyl group can be straight or branched. Examples of an alkynyl group include, but are not limited to, propargyl and butynyl. An alkynyl group can be optionally substituted with one or more substituents such as aroyl, heteroaroyl, alkoxy, cycloalkyloxy, heterocycloalkyloxy, aryloxy, heteroaryloxy, aralkyloxy, nitro, carboxy, cyano, halo, hydroxy, sulfo, mercapto, sulfanyl (e.g., aliphaticsulfanyl or cycloaliphaticsulfanyl), sulfinyl (e.g., aliphaticsulfinyl or cycloaliphaticsulfinyl), sulfonyl (e.g., aliphatic-SO2-, aliphaticamino-SO2-, or cycloaliphatic-SO2-), amido (e.g., aminocarbonyl, alkylaminocarbonyl, alkylcarbonylamino, cycloalkylaminocarbonyl, heterocycloalkylaminocarbonyl, cycloalkylcarbonylamino, arylaminocarbonyl, arylcarbonylamino, aralkylcarbonylamino, (heterocycloalkyl)carbonylamino, (cycloalkylalkyl) carbonylamino, heteroaralkylcarbonylamino, heteroarylcarbonylamino or heteroarylaminocarbonyl), urea, thiourea, sulfamoyl, sulfamide, alkoxycarbonyl, alkylcarbonyloxy, cycloaliphatic, heterocycloaliphatic, aryl, heteroaryl, acyl (e.g., (cycloaliphatic)carbonyl or (heterocycloaliphatic)carbonyl), amino (e.g., aliphaticamino), sulfoxy, oxo, carboxy, carbamoyl, (cycloaliphatic)oxy, (heterocycloaliphatic)oxy, or (heteroaryl)alkoxy.

The term "protecting group," as used herein, represents those groups intended to protect a functional group, such as, for example, an alcohol, amine, carboxyl, carbonyl, etc., against undesirable reactions during synthetic procedures. Commonly used protecting groups are disclosed in Greene and Wuts, Protective Groups in Organic Synthesis, 3rd Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are tert-butyloxycarbonyl (Boc).

Examples of useful protecting groups for acids are substituted alkyl esters such as 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, pivaloyloxymethyl, phenylacetoxymethyl, triisopropropylsysilylmethyl, cyanomethyl, acetol, phenacyl, substituted phenacyl esters, 2,2,2-trichloroethyl, 2-haloethyl, co-chloroalkyl, 2-(trimethylsilyl)ethyl, 2-methylthioethyl, t-butyl, 3-methyl-3-pentyl, dicyclopropylmethyl, cyclopentyl, cyclohexyl, allyl, methallyl, cynnamyl, phenyl, silyl esters, benzyl and substituted benzyl esters, 2,6-dialkylphenyl esters such as pentafluorophenyl, 2,6-dialkylpyhenyl. Preferred protecting groups for acids are methyl or ethyl esters.

Methods of adding (a process generally referred to as "protection") and removing (process generally referred to as "deprotection") such amine and acid protecting groups are well-known in the art and available, for example in P. J. Kocienski, Protecting Groups, Thieme, 1994, which is hereby incorporated by reference in its entirety and in Greene and Wuts, Protective Groups in Organic Synthesis, 3rd Edition (John Wiley & Sons, New York, 1999).

As used herein, the term, "leaving group" refers to an atom or group (charged or uncharged) that becomes detached from an atom in what is considered to be the residual or main part of the substrate in a specified reaction. For example, in the heterolytic solvolysis of benzyl bromide in acetic acid:

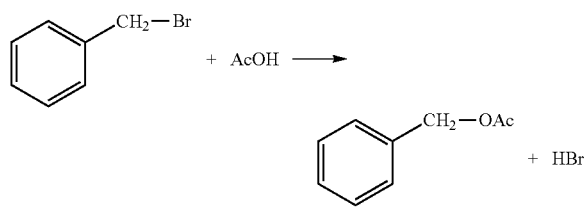

the leaving group is Br—; The term has meaning only in relation to a specified reaction. The leaving group is not, in general, the same as the substituent group present in the substrate (e.g. bromo and trimethylammonio in the substrates of the first two examples above.) A slightly different usage of the term prevails in the (non-mechanistic) naming of transformations, where the actual substituent group present in the substrate (and also in the product) is referred to as the leaving group (IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins).

The term "cycloaliphatic" refers to a monocyclic $C_{3-8}$ hydrocarbon or bicyclic $C_{7-12}$ hydrocarbon that is completely saturated or contains one or more units of unsaturation, but is not aromatic, and has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopentanyl, cyclopropenyl, and cyclobutyl. The term "heteroaliphatic", as used herein, means aliphatic groups wherein one or more chain carbon atoms are independently replaced by an oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups. The term "heterocycle", "heterocyclyl", and "heterocyclic" as used herein are interchangeable and mean non-aromatic, monocyclic, bicyclic, or tricyclic ring systems in which one or more ring members are an independently selected heteroatom. In some embodiments, the "heterocycle", "heterocyclyl", or "heterocyclic" group has three to fourteen ring members in which one or more ring members is a hetero atom independently selected from oxygen, sulfur, nitrogen, or phosphorus, and each ring in the system contains 3 to 7 ring members.

Examples of suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

Cyclic groups, (e.g., cycloaliphatic and heterocycles), can be linearly fused, bridged, or spirocyclic.

The term "heteroatom" or "hetero atom" means oxygen, sulfur, nitrogen, or phosphorus atom, including any oxidized form of nitrogen, sulfur, or phosphorus; the quarternized form of any basic nitrogen or; a substitutable nitrogen of a heterocyclic ring, e.g., N (as in 3,4-dihydro-2H-pyrrolyl), NH (as in pyrrolidinyl) or NR: (as in N-substituted pyrrolidinyl).

The term "unsaturated", as used herein, means that a moiety has one or more units of unsaturation.

The term "nonaromatic", as used herein, describes rings that are either saturated or partially unsaturated.

The term "aromatic", as used herein, describes rings that are fully unsaturated.

The term "alkoxy" or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl", "haloaliphatic", and "haloalkoxy" mean alkyl, alkenyl or alkoxy, as the case may be, substituted with one or more halogen atoms. The terms "halogen", "halo", and "hal" mean F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring."

An example of aryl is phenyl. Unless otherwise stated, aryl is optionally substituted and each of the optional substituents (e.g., 2 or 3 optional substituents) independently can be alkyl, halo, amino, alkoxy, haloalkyl, alkylsulfonyl, nitro, phenyl, piperazinyl (e.g., piperazin-1-yl or piperazin-4-yl), and 4-alkylpiperazin-1-yl.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more hetero atoms, and wherein each ring contains 3 to 7 ring members. The term "heteroaryl" may be used interchangeably with the term "heteroaryl ring" or "heteroaromatic". Examples of suitable heteroaryl include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 2-methylthiazol-4-yl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The terms "protecting group" and "protective group," as used herein, are interchangeable and refer to an agent used to temporarily block one or more desired reactive sites in a multifunctional compound. In certain embodiments, a protecting group has one or more, or preferably all, of the following characteristics: a) it is added selectively to a functional group in good yield to give a protected substrate that is b)

stable to reactions occurring at one or more of the other reactive sites; and c) is selectively removable in good yield by reagents that do not attack the regenerated, deprotected functional group. Exemplary protecting groups are detailed by T. W. Greene et al. in *Protective Groups in Organic Synthesis*, Third Edition, John Wiley & Sons, New York (1999) (and other editions of the book), the entire contents of which are incorporated herein by reference.

The term "nitrogen protecting group," as used herein, refers to an agent used to temporarily block one or more desired nitrogen reactive sites in a multifunctional compound. Suitable nitrogen protecting groups also possess the characteristics described above, and some examples nitrogen protecting groups are provided by T. W. Greene et al. in Chapter 7 of *Protective Groups in Organic Synthesis*, supra.

In some embodiments, an alkyl or aliphatic chain can be optionally interrupted with another atom or group. This means that a methylene unit of the alkyl or aliphatic chain is optionally replaced with the other atom or group. Examples of such other atom or group include, but are not limited to, —NR—, —O—, —S—, —CO$_2$—, —OC(O)—, —C(O)CO—, —C(O)—, —C(O)NR—, —C(=N—CN)—, —NRCO—, —NRC(O)O—, —SO$_2$NR—, —NRSO$_2$—, —NRC(O)NR—, —OC(O)NR—, —NRSO$_2$NR—, —SO—, or —SO$_2$—, wherein R is defined herein. Unless otherwise specified, the optional replacements form a chemically stable compound. Optional interruptions can occur within the chain or at either end of the chain; i.e., both at the point of attachment or also at a terminal end. Two optional replacements can also be adjacent to each other within a chain as long as it results in a chemically stable compound. The optional interruptions or replacements can also completely replace all of the carbon atoms in a chain. For example, a C$_3$ aliphatic can be optionally interrupted or replaced by —NR—, —C(O)—, and —NR— to form —NRC(O)NR— (urea). Unless otherwise specified, if the replacement or interruption occurs at a terminal end, the replacement atom is bound to an H on the terminal end. For example, if —CH$_2$CH$_2$CH$_3$ is optionally interrupted with —O—, the resulting compound could be —OCH$_2$CH$_3$, —CH$_2$OCH$_3$, or —CH$_2$CH$_2$OH.

Unless otherwise stated, a substituent can freely rotate around any rotatable bonds. For example, a substituent drawn as

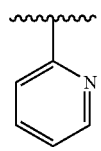

also represents

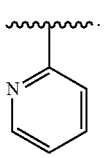

Additionally, unless otherwise stated, structures depicted or described herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The following abbreviations are used here:

PG protecting group
LG leaving group
DCM dichloromethane
Ac acetyl
DMF dimethylformamide
EtOAc ethyl acetate
DMSO dimethyl sulfoxide
MeCN acetonitrile
TCA trichloroacetic acid
ATP adenosine triphosphate
EtOH ethanol
Ph phenyl
Me methyl
Et ethyl
Bu butyl
DEAD diethylazodicarboxylate
HEPES 4-(2-hydroxyethyl)-1-piperazineethanesulfonic acid
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography General Synthetic Methods The compounds of this invention may be prepared in general by methods known to those skilled in the art such as, e.g., those depicted in the general schemes below. Unless otherwise indicated, all variables in the following schemes are as defined herein. These compounds may be analyzed by known methods such as, e.g., MS (mass spectrometry), LCMS (liquid chromatography mass spectrometry), and NMR (nuclear magnetic resonance).

In one method, compounds of the invention wherein Y is O may be prepared as illustrated in Scheme 1.

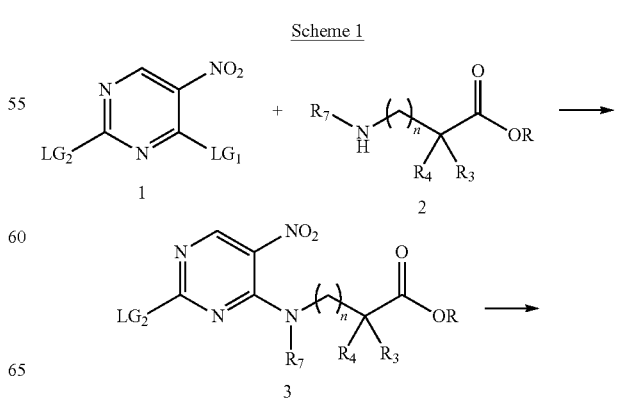

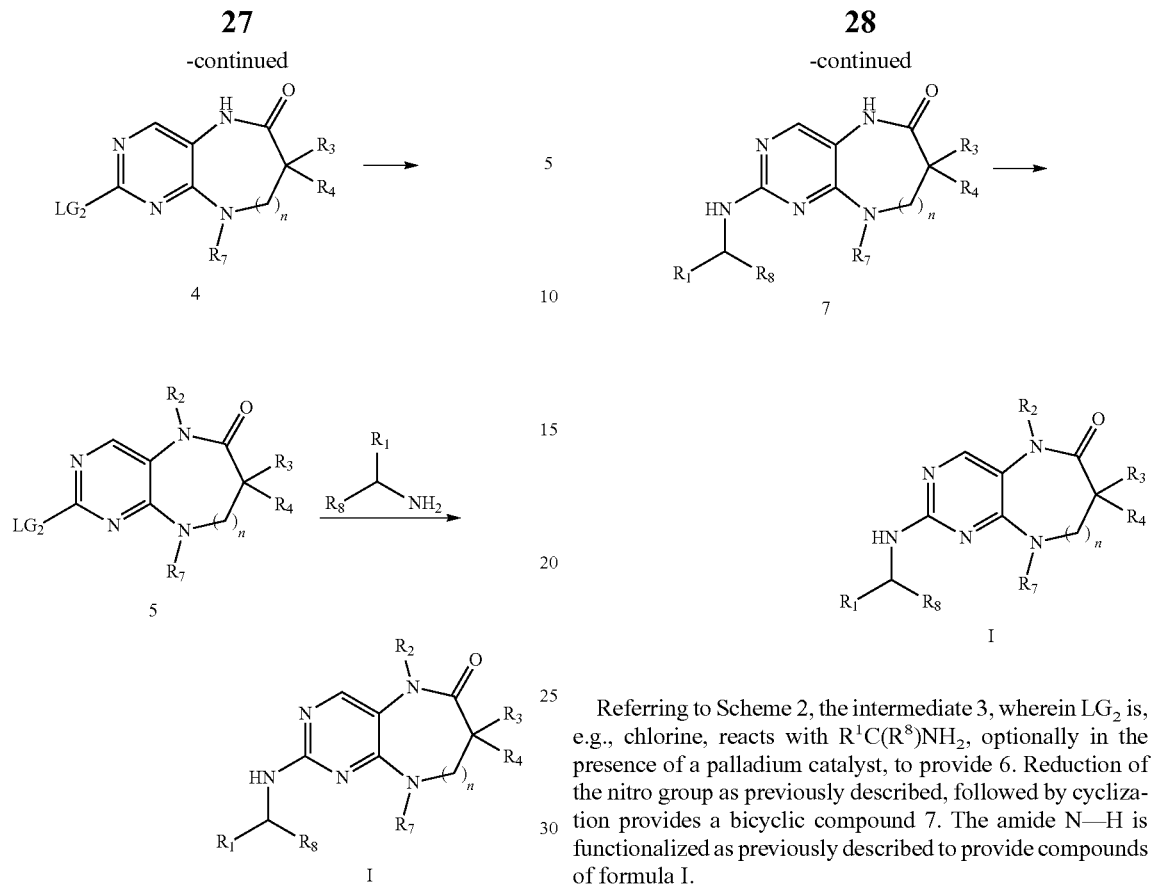

Referring to Scheme 1, the nitro pyrimidine 1, wherein LG₁ and LG₂ are, e.g., chlorine, reacts with α- or β-aminoesters 2 (when n is 0 or 1) to provide an adduct 3. Reduction of the nitro group under known conditions, followed by cyclization, provides a bicyclic compound 4. The amide N—H may be functionalized by reaction with, e.g., an alkyl halide in the presence of a strong base such as, e.g., sodium hydride to provide compound 5. Reaction of compound 5 with R¹C(R⁸)NH₂, optionally in the presence of a palladium catalyst, provides compounds of Formula I.

An alternative method for preparing compounds of Formula I is shown in Scheme 2.

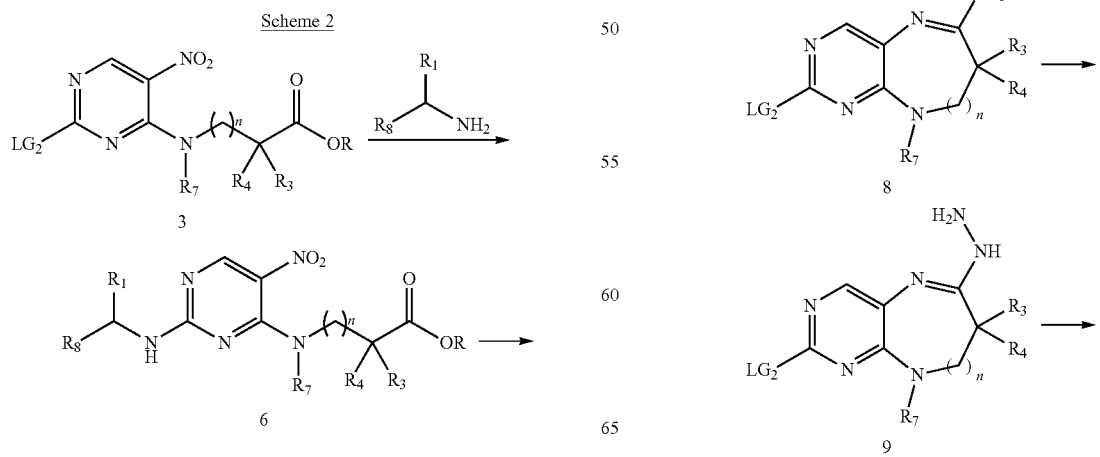

Referring to Scheme 2, the intermediate 3, wherein LG₂ is, e.g., chlorine, reacts with R¹C(R⁸)NH₂, optionally in the presence of a palladium catalyst, to provide 6. Reduction of the nitro group as previously described, followed by cyclization provides a bicyclic compound 7. The amide N—H is functionalized as previously described to provide compounds of formula I.

Preparation of compounds of this invention in which Y is NR⁹, and R⁹ and R² together with the atoms to which they are attached form a triazole ring is shown in Scheme 3.

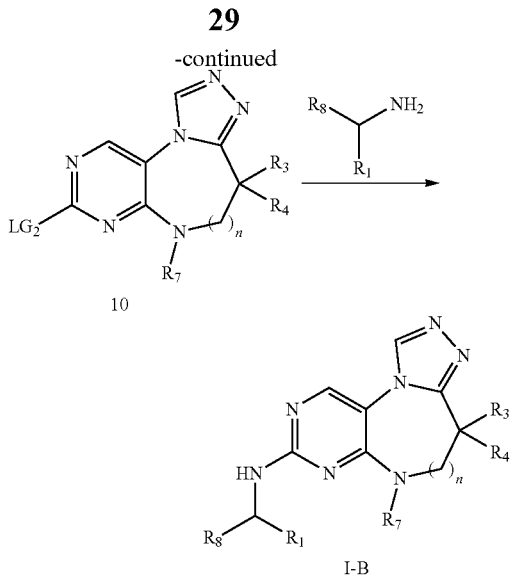

I-B

Referring to Scheme 3, activation of the lactam functional group in compound 4 provides an intermediate 8 wherein $LG_3$ is, e.g., chlorine, followed by displacement with hydrazine provides a second intermediate 9. Reaction of intermediate 9 with an orthoformate ester (e.g., methyl orthoformate) provides a triazole intermediate 10. Reaction of intermediate 10 with $R^1C(R^8)NH_2$ as previously described provides a compound of Formula I-B.

The compounds of this invention in general are potent inhibitors of protein kinases such as PLKs, e.g., PLK1, pLK2, PLK3, or PLK4. In some instances, the compounds of this invention demonstrate PLK1 inhibition at concentrations of less than 10 nM. In other instances, the compounds of this invention demonstrate PLK1 inhibition at concentrations of less than 1 nM. Further, the compounds of the invention demonstrate advantageous pharmaco-kinetic properties.

As potent inhibitors of protein kinases (e.g., PLKs such as PLK1 or PLK2), the compounds of this invention and compositions containing the same are useful for treating or lessening the severity or indications of a disease, disorder, or condition wherein a protein kinase (e.g., PLKs such as PLK1 or PLK2) is implicated. Accordingly, the invention includes methods for treatment, lessening the severity or indications, or prevention of such diseases, disorders, or conditions with compounds of compositions of this invention.

Examples of such diseases, disorders, or conditions include, but are not limited to, autoimmune diseases, inflammatory diseases, proliferative diseases, hyperproliferative diseases, immunologically-mediated diseases, bone diseases, metabolic diseases, neurological diseases, neurodegenerative diseases, cardiovascular diseases, hormone related diseases, allergies, asthma, and Alzheimer's disease.

Depending upon the particular protein kinase-mediated disease, disorder, or condition to be treated or prevented, one or more additional drugs, which are normally administered to treat or prevent that disease, disorder, or condition may be administered together with the inhibitors of this invention. For example, chemotherapeutic agents or other anti-proliferative agents may be combined with the compounds of this invention to treat proliferative diseases.

Those additional agents may be administered separately, as part of a multiple dosage regimen, from the compounds of this invention or pharmaceutical compositions containing them. Alternatively, one or more of those additional agents may be part of a single dosage faun, mixed together with a compound of this invention in a single composition.

As inhibitors of protein kinases, the compounds and compositions of this invention are also useful in biological samples. One aspect of the invention relates to inhibiting protein kinase activity in a biological sample, which includes contacting the biological sample with a compound of Formula I or a composition containing the compound. The term "biological sample", as used herein, means an in vitro or an ex vivo sample. Examples of biological samples include, but are not limited to, cell cultures, biopsied material obtained from a mammal, blood, saliva, urine, feces, semen, tears, or other body fluids, or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Accordingly, another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radio-labeling the inhibitor prior to binding, isolating the inhibitor/kinase complex and determining the amount of radiolabel bound, or by running a competition experiment where new inhibitors are incubated with the kinase bound to known radio-ligands. Detailed conditions for assaying a compound utilized in this invention as an inhibitor of PLK1, PLK2, PLK3, and PLK4 are set forth in the Examples below.

Set forth below are some specific examples of the compounds of this invention, and their preparation and assays for activities. It should be understood that these examples and specific conditions illustrated and described below are demonstrative only, and should not be construed to limit the scope of this invention.

Example 1

(S)-9-cyclopentyl-5,7,7-trimethyl-2-(1-phenylethylamino)-8,9-dihydro-5H-pyrimido[4,5-b][1,4]diazepin-6(7H)-one 2-Chloro-9-cyclopentyl-5,7,7-trimethyl-8,9-dihydro-5H-pyrimido[5,4-b][1,4]diazepin-6(7H)-one (100 mg, 0.3238 mmol, prepared as described in WO 2007/095188) was dissolved in n-butyl alcohol (1 mL). To the butyl alcohol solution thus obtained were then added (1S)-1-phenylethanamine (750 µL, 5.830 mmol) and DIPEA (167.4 mg, 225.6 µL, 1.295 mmol). The resulting solution was heated at 140° C. in microwave for 90 minutes. Additional (1S)-1-phenylethanamine (500 µL, 3.887 mmol) was added and the reaction mixture heated for 90 minutes in microwave at 140° C. The solvent was removed in vacuo and the residue dissolved in dichloromethane and washed sequentially with 0.5M HCl (three times, 5 mL each), saturated aqueous sodium hydrogen carbonate solution (three times, 5 mL each), and brine (once, 5 mL). The washed solution was dried over $MgSO_4$, filtered, and concentrated in vacuo to give yellow oil. The oil was purified by mass directed HPLC and the product fractions passed through a bicarbonate cartridge and lypholized to afford the title compound as a white solid (33.5 mg, 26% yield).

$^1$H NMR (DMSO-d$_6$, 400 MHz): δ 1.01 (d, 6H), 1.38 (d, 3H), 1.38-1.48 (m, 2H), 1.52-1.68 (m, 4H), 1.77-1.97 (m, 1H), 3.08 (s, 3H), 3.15-3.25 (m, 2H), 4.84 (br s, 2H), 7.14-7.18 (m, 2H), 7.24-7.28 (m, 2H), 7.31-7.34 (m, 2H), 7.37 (s, 1H).

MS (ES+) 394, (ES−) 392.

Shown in the following table are other compounds that were prepared by a method similar to that used for preparing Example 1.

| Example No. | Name of Compound | Physical Data |
|---|---|---|
| 2 | (S)-9-cyclopentyl-5,7,7-trimethyl-2-(1-phenylpropylamino)-8,9-dihydro-5H-pyrimido[4,5-b][1,4]diazepin-6(7H)-one | $^1$H NMR (DMSO-d$_6$, 400 MHz): δ 0.86 (s, 3H), 1.01 (s, 6H), 1.23-1.70 (m, 8H), 1.78-1.83 (m, 2H), 3.08 (s, 3H), 3.14-3.26 (m, 2H), 4.60 (br s, 1H), 5.00 (br s, 1H), 7.16-7.30 (m, 6H), 7.72 (br s, 1H). MS (ES+) 408, (ES−) 406. |
| 3 | (R)-9-cyclopentyl-2-(2-methoxy-1-phenylethylamino)-5,7,7-trimethyl-8,9-dihydro-5H-pyrimido[4,5-b][1,4]diazepin-6(7H)-one | $^1$H NMR (DMSO-d$_6$, 400 MHz): δ 1.02 (s, 6H), 1.41-1.75 (m, 7H), 1.87-1.92 (m, 1H), 3.09 (s, 3H), 3.17-3.22 (m, 2H), 3.23 (s, 3H), 3.41-3.62 (m, 3H), 5.05-5.10 (br m, 1H), 7.02 (br s, 1H), 7.17-7.42 (m, 5H), 7.75 (s, 1H). MS (ES+) 424, (ES−) 422. |
| 4 | (R)-9-cyclopentyl-2-(2-hydroxy-1-phenylethylamino)-5,7,7-trimethyl-8,9-dihydro-5H-pyrimido[4,5-b][1,4]diazepin-6(7H)-one | $^1$H NMR (DMSO-d$_6$, 400 MHz): δ 1.01 (s, 6H), 1.36-1.68 (m, 7H), 1.83-1.86 (m, 1H), 3.09 (s, 3H), 3.18-3.26 (m, 2H), 3.58 (s, 2H), 4.86 (br m, 2H), 6.84 (m, 1H), 7.18-7.35 (m, 6H), 7.75 (s, 1H). MS (ES+) 410, (ES−) 408. |
| 5 | (S)-2-(1-(4-bromophenyl)ethylamino)-9-cyclopentyl-5,7,7-trimethyl-8,9-dihydro-5H-pyrimido[4,5-b][1,4]diazepin-6(7H)-one | $^1$H NMR (DMSO-d$_6$, 400 MHz): δ 1.01 (d, 6H), 1.37 (d, 3H), 1.36-1.46 (m, 4H), 1.47-1.65 (m, 3H), 1.75-1.82 (m, 1H), 3.09 (s, 3H), 3.17-3.26 (m, 2H), 4.81 (br s, 2H), 7.18 (br s, 1H), 7.28 (d, 2H), 7.46 (d, 2H), 7.74 (s, 1H). MS (ES+) 472, (ES−) 470. |
| 7 | (S)-9-cyclopentyl-5,7,7-trimethyl-2-(1-p-tolylethylamino)-8,9-dihydro-5H-pyrimido[4,5-b][1,4]diazepin-6(7H)-one | $^1$H NMR (DMSO-d$_6$, 400 MHz): δ 1.02 (d, 6H), 1.36 (d, 3H), 1.24-1.48 (m, 4H), 1.62-1.69 (m, 3H), 1.80-1.85 (m, 1H), 2.24 (s, 3H), 3.08 (s, 3H), 3.19-3.25 (m, 2H), 4.81-5.09 (br m, 2H), 7.07 (m, 3H), 7.21 (d, 2H), 7.73 (s, 1H). MS (ES+) 408, (ES−) 406. |
| 8 | (S)-2-(1-(4-chlorophenyl)ethylamino)-9-cyclopentyl-5,7,7-trimethyl-8,9-dihydro-5H-pyrimido[4,5-b][1,4]diazepin-6(7H)-one | 1H NMR (DMSO-d6, 400 MHz) δ 1.01 (d, 6H), 1.37 (d, 4H), 1.40-1.50 (m, 2H), 1.50-1.65 (m, 4H), 1.75-1.85 (m, 1H), 3.09 (s, 3H), 3.10-3.22 (m, 2H), 4.75-4.89 (m, 2H), 7.16 (br s, 1H), 7.33 (s, 4H), 7.74 (s, 1H). MS (ES+) 428, (ES−) 426. |
| 9 | (S)-9-cyclopentyl-2-(1-(4-fluorophenyl)ethylamino)-5,7,7-trimethyl-8,9-dihydro-5H-pyrimido[4,5-b][1,4]diazepin-6(7H)-one | 1H NMR (DMSO-d6, 400 MHz) δ 1.01 (s, 6H), 1.38-1.49 (m, 7H), 1.50-1.65 (m, 3H), 1.81-1.90 (m, 1H), 3.09 (s, 3H), 3.15-3.26 (m, 2H), 4.86 (br s, 2H), 7.07-7.14 (m, 3H), 7.33-7.37 (m, 2H), 7.74 (s, 1H). MS (ES+) 412, (ES−) 410. |
| 10 | (S)-9-cyclopentyl-2-(1-(4-methoxyphenyl)ethylamino)-5,7,7-trimethyl-8,9-dihydro-5H-pyrimido[4,5-b][1,4]diazepin-6(7H)-one | $^1$H NMR (DMSO-d$_6$, 400 MHz): δ 1.02 (d, 6H), 1.35-1.65 (m, 11H), 3.09 (s, 3H), 3.23 (m, 2H), 3.70 (s, 3H), 4.81 (br s, 1H), 4.98 (m, 1H), |

| Example No. | Name of Compound | Physical Data |
|---|---|---|
| | | 6.82 (m, 2H), 7.04 (m, 1H), 7.23 (m, 2H), 7.73 (1H, s). MS (ES+) 424, (ES−) 422. |
| 11 | (S)-9-cyclopentyl-2-(1-(3-methoxyphenyl)ethylamino)-5,7,7-trimethyl-8,9-dihydro-5H-pyrimido[4,5-b][1,4]diazepin-6(7H)-one | $^1$H NMR (DMSO-$d_6$, 400 MHz): δ 1.02 (d, 6H), 1.38 (d, 4H), 1.44-1.48 (m, 3H), 1.58-1.63 (m, 3H), 1.80-1.90 (m, 1H), 3.09 (s, 3H), 3.11-3.28 (m, 2H), 3.71 (s, 3H), 4.78-5.00 (m, 2H), 6.72-6.74 (m, 1H), 6.91 (s, 2H), 7.18 (t, 2H), 7.74 (s, 1H). MS (ES+) 424, (ES−) 422. |
| 12 | (S)-9-cyclopentyl-2-(1-(2-methoxyphenyl)ethylamino)-5,7,7-trimethyl-8,9-dihydro-5H-pyrimido[4,5-b][1,4]diazepin-6(7H)-one | $^1$H NMR (DMSO-$d_6$, 400 MHz): δ 1.00 (s, 6H), 1.31 (d, 3H), 1.24-1.64 (m, 8H), 1.79-1.85 (m, 1H), 3.09 (s, 3H), 3.17-3.24 (m, 2H), 3.82 (s, 3H), 4.75 (br s, 1H), 5.25 (br s, 1H), 6.84 (t, 1H), 6.94 (d, 1H), 7.13 (t, 1H), 7.27 (d, J = 8.0 Hz, 1H), 7.73 (s, 1H). MS (ES+) 424, (ES−) 423. |
| 13 | (S)-9-cyclopentyl-5,7,7-trimethyl-2-(1-(2-(trifluoromethyl)phenyl)ethylamino)-8,9-dihydro-5H-pyrimido[4,5-b][1,4]diazepin-6(7H)-one | $^1$H NMR (DMSO-$d_6$, 400 MHz): δ 0.99 (d, 6H), 1.18-1.28 (m, 2H), 1.30-1.45 (m, 6H), 1.50-1.65 (m, 2H), 1.68-1.78 (m, 1H), 3.08 (s, 3H), 3.18 (s, 2H), 5.05 (br s, 1H), 5.30 (br s, 1H), 7.26 (d, 1H), 7.41 (d, 1H), 7.61-7.67 (m, 2H), 7.75 (s, 1H), 7.80 (d, 1H). MS (ES+) 462, (ES−) 460. |
| 14 | (S)-9-cyclopentyl-5,7,7-trimethyl-2-(1-(4-nitrophenyl)ethylamino)-8,9-dihydro-5H-pyrimido[4,5-b][1,4]diazepin-6(7H)-one | $^1$H NMR (DMSO-$d_6$, 400 MHz): δ 1.00 (d, 6H), 1.20-1.45 (m, 7H), 1.50-1.70 (m, 3H), 1.75-1.85 (m, 1H), 3.08 (s, 3H), 3.12-3.22 (m, 2H), 4.70 (br s, 1H), 4.95 (br s, 1H), 7.33 (s, 1H), 7.59 (d, 2H), 7.75 (s, 1H), 8.17 (d, 2H). MS (ES+) 439, (ES−) 437. |
| 15 | (RS)-9-cyclopentyl-5,7,7-trimethyl-2-(1-(4-(methylsulfonyl)phenyl)ethylamino)-8,9-dihydro-5H-pyrimido[4,5-b][1,4]diazepin-6(7H)-one | $^1$H NMR (DMSO-$d_6$, 400 MHz): δ 1.00 (d, 6H), 1.41 (d, 6H), 1.51-1.71 (m, 3H), 1.78-1.88 (m, 1H), 3.08 (s, 3H), 3.16 (s, 3H), 3.18-3.24 (m, 2H), 4.90 (br s, 1H), 7.30 (br s, 1H), 7.58 (d, 2H), 7.75 (s, 1H), 7.84 (d, 2H). MS (ES+) 472, (ES−) 470. |
| 16 | (RS)-2-(1-(biphenyl-4-yl)ethylamino)-9-cyclopentyl-5,7,7-trimethyl-8,9-dihydro-5H-pyrimido[4,5-b][1,4]diazepin-6(7H)-one | $^1$H NMR (DMSO-$d_6$, 400 MHz): δ 1.06 (d, 6H), 1.25-1.50 (m, 4H), 1.60-1.72 (m, 4H), 1.90-2.00 (m, 1H), 3.13-3.32 (m, 5H), 4.95-5.05 (m, 2H), 5.15 (br s, 1H), 7.34-7.37 (m, 1H), 7.46-7.50 (m, 4H), 7.51-7.62 (m, 4H), 7.63 (s, H), 7.73 (s, 1H). MS (ES+) 470, (ES−) 468. |
| 17 | (RS)-9-cyclopentyl-5,7,7-trimethyl-2-(1-(naphthalen-1-yl)ethylamino)-8,9-dihydro-5H-pyrimido[4,5-b][1,4]diazepin-6(7H)-one | $^1$H NMR (DMSO-$d_6$, 400 MHz): δ 0.95-1.00 (m, 1H), 1.01 (d, 6H), 1.19-1.38 (m, 3H), 1.39-1.48 (m, 2H), 1.58 (d, 4H), 3.05 (d, 1H), 3.05-3.15 (m, 2H), 3.15 (s, 3H), 4.55 (br s, 1H), 5.35 (br s, 1H), 5.75-5.82 (m, 1H), 7.41-7.59 (m, 3H), 7.62 (d, 1H), 7.70-7.80 (m, 2H), 7.91 (d, 1H), 8.20 (d, 1H). MS (ES+) 444, (ES−) 442. |

-continued

| Example No. | Name of Compound | Physical Data |
|---|---|---|
| 18 | (RS)-9-cyclopentyl-5,7,7-trimethyl-2-(1-(pyridin-3-yl)ethylamino)-8,9-dihydro-5H-pyrimido[4,5-b][1,4]diazepin-6(7H)-one | $^1$H NMR (DMSO-$d_6$, 400 MHz): δ 1.35-1.51 (m, 8H), 1.51-1.75 (m, 2H), 1.78-1.84 (m, 1H), 3.10 (s, 3H), 3.11-3.25 (m, 2H), 4.89-4.92 (m, 2H), 7.22 (s, 1H), 7.28-7.31 (m, 1H), 7.71-7.75 (m, 2H), 8.38 (m, 1H), 8.54 (s, 1H). MS (ES+) 395, (ES−) 393. |
| 19 | (RS)-9-cyclopentyl-5,7,7-trimethyl-2-(1-(pyridin-4-yl)ethylamino)-8,9-dihydro-5H-pyrimido[4,5-b][1,4]diazepin-6(7H)-one | $^1$H NMR (DMSO-$d_6$, 400 MHz): δ 1.00 (s, 6H), 1.29 (d, 3H), 1.28-1.40 (m, 4H), 1.54-1.67 (m, 3H), 1.74-1.88 (m, 1H), 3.09 (s, 3H), 3.20-3.27 (m, 2H), 4.80-4.90 (br s, 2H), 7.25 (br s, 1H), 7.31 (d, 2H), 7.75 (s, 1H), 8.44 (d, 2H). MS (ES+) 395, (ES−) 393. |
| 20 | (RS)-9-cyclopentyl-2-(1-(furan-2-yl)ethylamino)-5,7,7-trimethyl-8,9-dihydro-5H-pyrimido[4,5-b][1,4]diazepin-6(7H)-one | $^1$H NMR (DMSO-$d_6$, 400 MHz): δ 1.05 (s, 6H), 1.42 (d, 3H), 1.48-1.59 (m, 4H), 1.61-1.74 (m, 3H), 1.79-1.87 (m, 1H), 3.12 (s, 3H), 3.27 (s, 2H), 4.99-5.15 (br m, 2H), 6.13 (s, 1H), 6.34 (s, 1H), 6.89 (br d, 1H), 7.51 (s, 1H), 7.78 (s, 1H). MS (ES+) 384. |
| 21 | (RS)-9-cyclopentyl-2-(1-(3,4-dimethoxyphenyl)ethylamino)-5,7,7-trimethyl-8,9-dihydro-5H-pyrimido[4,5-b][1,4]diazepin-6(7H)-one | $^1$H NMR (DMSO-$d_6$, 400 MHz): δ 1.02 (d, 6H), 1.37 (d, 3H), 1.40-1.72 (m, 7H), 1.80-1.88 (m, 1H), 3.09 (s, 3H), 3.17-3.27 (m, 2H), 3.70 (s, 3H), 3.72 (s, 3H), 4.84-5.03 (br m, 2H), 6.83 (s, 2H), 6.97 (s, 1H), 7.02 (br s, 1H), 7.74 (s, 1H). MS (ES+) 454, (ES−) 452. |
| 22 | (RS)-9-cyclopentyl-5,7,7-trimethyl-2-(1-(4-(trifluoromethoxy)phenyl)ethylamino)-8,9-dihydro-5H-pyrimido[4,5-b][1,4]diazepin-6(7H)-one | $^1$H NMR (DMSO-$d_6$, 400 MHz) δ 1.00 (s, 6H), 1.39 (d, 3H), 1.34-1.46 (m, 4H), 1.50-1.72 (m, 3H), 1.74-1.84 (m, 1H), 3.09 (s, 3H), 3.14-3.21 (m, 2H), 4.80-4.96 (br m, 2H), 7.20 (br s, 1H), 7.27 (d, 2H), 7.43 (d, 2H), 7.75 (s, 1H). MS (ES+) 478 (ES−) 476. |
| 23 | (R)-N-((S)-1-(4-bromophenyl)ethyl)-5-cyclopentyl-4-ethyl-4,5-dihydro-[1,2,4]triazolo[4,3-f]pteridin-7-amine [from (6R)-3-chloro-5-cyclopentyl-6-ethyl-6H-imidazo[1,2-f]pteridine, synthesized as described in WO 2007/120752] | $^1$H NMR (CDCl$_3$, 400 MHz): δ 0.8-0.9 (m, 3H), 1.6-1.9 (m, 11H), 2.1-2.15 (m, 3H), 4.18-4.25 (m, 1H), 4.9-5.0 (m, 1H), 5.2-5.25 (m, 1H), 7.25 (d, 2H), 7.45 (d, 2H), 8.9 (s, 1H), 8.98-9.08 (m, 2H). MS (ES+) 470, (ES−) 468. |
| 24 | (R)-5-cyclopentyl-4-ethyl-N-((S)-1-phenylethyl)-4,5-dihydro-[1,2,4]triazolo[4,3-f]pteridin-7-amine | $^1$H NMR (CDCl$_3$, 400 MHz): δ 0.8-0.9 (m, 3H), 1.5-2.2 (m, 14H), 4.2-4.3 (m, 1H), 5.0-5.1 (m, 2H), 5.38-5.45 (m, 1H), 7.2-7.4 (m, 5H), 8.05 (s, 1H), 8.5 (s, 1H). MS (ES+) 390, (ES−) 388. |
| 25 | (R)-8-cyclopentyl-7-ethyl-5-methyl-2-((S)-1-phenylethylamino)-7,8-dihydropteridin-6(5H)-one [from (R)-2-chloro-8-cyclopentyl-7-ethyl-5-methyl-7,8-dihydropteridin-6(5H)-one, synthesized as described in US 2004/176380] | $^1$H NMR (CDCl$_3$, 400 MHz) δ 0.8-0.9 (m, 3H), 1.5-1.9 (m, 12H), 2.0-2.1 (m, 1H), 3.25 (s, 3H), 4.1-4.2 (m, 2H), 5.0-5.1 (m, 1H), 5.18-5.25 (m, 1H), 7.2-7.4 (m, 5H), 7.5 (s, 1H); MS (ES+) 380, (ES−) 378. |

| Example No. | Name of Compound | Physical Data |
|---|---|---|
| 27 | (R,S)-9-cyclopentyl-5,7,7-trimethyl-2-(1-(2-methylthiazol-4-yl)ethylamino)-8,9-dihydro-5H-pyrimido[4,5-b][1,4]diazepin-6(7H)-one | $^1$H NMR (DMSO-$d_6$, 400 MHz): δ 1.05 (d, 6H), 1.43 (d, 3H), 1.42-1.55 (m, 4H), 1.58-1.67 (m, 3H), 1.74-1.83 (m, 1H), 2.61 (s, 3H), 3.11 (s, 3H), 3.25-3.28 (m, 2H), 5.04 (br s, 2H), 6.87 (br s, 1H), 7.05 (s, 1H), 7.77 (s, 1H). MS (ES+) 415, (ES−) 413. |
| 28 | (S)-9-cyclopentyl-5,7,7-trimethyl-2-(1-(3-(trifluoromethyl)phenyl)ethylamino)-8,9-dihydro-5H-pyrimido[4,5-b][1,4]diazepin-6(7H)-one | $^1$H NMR (DMSO-$d_6$, 400 MHz): δ 0.87 (d, 6H), 1.28 (d, 3H), 1.25-1.60 (m, 7H), 1.65-1.72 (m, 1H), 2.96 (s, 3H), 3.02-3.12 (m, 2H), 4.82 (br s, 2H), 7.15 (br s, 1H), 7.40 (d, 2H), 7.50-7.53 (m, 2H), 7.62 (s, 1H). MS (ES+) 462, (ES−) 460. |
| 29 | (R,S)-9-cyclopentyl-2-(1-(2-fluorophenyl)ethylamino)-5,7,7-trimethyl-8,9-dihydro-5H-pyrimido[4,5-b][1,4]diazepin-6(7H)-one | $^1$H NMR (DMSO-$d_6$, 400 MHz): δ 1.00 (s, 6H), 1.38 (d, 3H), 1.30-1.50 (m, 4H), 1.52-1.65 (m, 3H), 1.77-1.83 (m, 1H), 3.09 (s, 3H), 3.14-3.25 (m, 2H), 4.89 (br s, 1H), 5.19 (br s, 1H), 7.10-7.13 (m, 2H), 7.19-7.22 (m, 2H), 7.39-7.42 (m, 1H), 7.75 (s, 1H). MS (ES+) 412, (ES−) 410. |
| 30 | (R,S)-9-cyclopentyl-2-(1-(3,5-difluorophenyl)ethylamino)-5,7,7-trimethyl-8,9-dihydro-5H-pyrimido[4,5-b][1,4]diazepin-6(7H)-one | $^1$H NMR (DMSO-$d_6$, 400 MHz): δ 1.01 (s, 6H), 1.38 (d, 3H), 1.37-1.50 (m, 4H), 1.54-1.65 (m, 3H), 1.78-1.88 (m, 1H), 3.10 (s, 3H), 3.16-3.25 (m, 2H), 4.09 (br s, 2H), 6.97-7.04 (m, 3H), 7.21 (br s, 1H), 7.76 (s, 1H). MS (ES+) 430, (ES−) 428. |
| 31 | (S)-9-cyclopentyl-5,7,7-trimethyl-2-(1-(4-(trifluoromethyl)phenyl)ethylamino)-8,9-dihydro-5H-pyrimido[4,5-b][1,4]diazepin-6(7H)-one | $^1$H NMR (DMSO-$d_6$, 400 MHz): δ 1.00 (d, 6H), 1.41 (d, 3H), 1.15-1.47 (m, 4H), 1.39-1.68 (m, 3H), 1.73-1.82 (m, 1H), 3.09 (s, 3H), 3.15-3.26 (m, 2H), 4.89 (br s, 2H), 7.26 (br s, 1H), 7.54 (d, 2H), 7.65 (d, 2H), 7.75 (s, 1H). MS (ES+) 462, (ES−) 460. |
| 32 | (S)-2-(1-(3,5-bis(trifluoromethyl)phenyl)ethylamino)-9-cyclopentyl-5,7,7-trimethyl-8,9-dihydro-5H-pyrimido[4,5-b][1,4]diazepin-6(7H)-one | $^1$H NMR (DMSO-$d_6$, 400 MHz): δ 0.96 (s, 3H), 1.01 (s, 3H), 1.45 (d, 3H), 1.12-1.60 (m, 7H), 1.75-1.83 (m, 1H), 3.09 (s, 3H), 3.20 (s, 2H), 4.81 (br s, 1H), 5.07 (br s, 1H), 7.37 (br s, 1H), 7.78 (s, 1H), 7.92 (s, 1H), 8.02 (s, 2H). MS (ES+) 530, (ES−) 528. |
| 33 | (R)-4-ethyl-5-phenyl-N-((S)-1-phenylethyl)-4,5-dihydro-[1,2,4]triazolo[4,3-f]pteridin-7-amine [from (6R)-3-chloro-6-ethyl-5-phenyl-6H-imidazo[1,2-f]pteridine, synthesized as described in WO2007120752] | $^1$H NMR (DMSO-$d_6$, 400 MHz): δ 0.73 (t, 3H), 1.30 (d, 3H), 1.66-1.76 (m, 1H), 1.91-1.94 (m, 1H), 4.49 (br s, 1H), 5.49 (br s, 1H), 6.69 (br s, 1H), 7.04 (br s, 3H), 7.44 (d, 5H), 7.56 (s, 2H), 8.46 (s, 1H), 9.21 (s, 1H); MS (ES+) 398, (ES−) 396. |
| 34 | 5-cyclopentyl-4-(R)-ethyl-N-((S)1-(4-(4-methylpiperazin-1-yl)phenyl)ethyl)-4,5-dihydro-[1,2,4]triazolo[4,3-f]pteridin-7-amine | $^1$H NMR (CDCl$_3$, 400 MHz): δ 0.85-0.95 (m, 3H), 1.3-1.4 (m, 3H), 1.45-1.8 (m, 14H), 1.9-2.0 (m, 1H), 2.0-2.1 (m, 1H), 2.3-2.4 (m, 2H), 2.6-2.7 (m, 2H), 3.2-3.3 (m, 2H), 4.3-4.4 (m, 1H), 5.0-5.1 (m, 2H), 5.25-5.35 (m, 1H), 6.9-6.96 (m, 1H), 7.25-7.35 (m, 2H), 8.1 (s, 1H), 8.5 (s, 1H). MS (ES+) 488.1 (ES−) 488.1 |

-continued

| Example No. | Name of Compound | Physical Data |
|---|---|---|
| 35 | 5-cyclopentyl-4-(R)-ethyl-N-((S)1-(4-(piperazin-1-yl)phenyl)ethyl)-4,5-dihydro-[1,2,4]triazolo[4,3-f]pteridin-7-amine | $^1$H NMR (CDCl$_3$, 400 MHz): δ 0.67-0.71 (m, 3H), 1.44 (m, 3H), 1.42-1.92 (m, 11H), 3.22-3.26 (m, 8H), 4.95 (b s, 1H), 5.15 (br s, 1H), 6.92-6.96 (m, 2H), 7.22-7.24 (m, 2H), 8.42 (br s, 1H), 8.66 (m, 2H), 9.16 (s, 1H). MS (ES+) 474.1 |

Example 6

(S)-9-cyclopentyl-5,7,7-trimethyl-2-(1-(4-(4-methylpiperazin-1-yl)phenyl)ethylamino)-8,9-dihydro-5H-pyrimido[4,5-b][1,4]diazepin-6(7H)-one (S)-2-(1-(4-Bromophenyl)ethylamino)-9-cyclopentyl-5,7,7-trimethyl-8,9-dihydro-5H-pyrimido[4,5-b][1,4]diazepin-6(7H)-one (100 mg, 0.2117 mmol), 1-methylpiperazine (84.82 mg, 93.93 µL, 0.8468 mmol), di-tert-butyl-(2-phenylphenyl)phosphane (6.317 mg, 0.02117 mmol) and K$_3$PO$_4$ (89.87 mg, 0.4234 mmol) were taken in up DME (2 mL) and degassed using cycles of vacuum and nitrogen. Pd$_2$ DBA$_3$ (19.39 mg, 0.02117 mmol) was added and the reaction mixture was further degassed and then heated at 100° C. in a sealed tube for 4 hours and then allowed to cool to the ambient temperature. The reaction mixture was then diluted with ethyl acetate (5 mL) and filtered. The filtrate was concentrated in vacuo and the residue purified by mass directed HPLC and the combined product fractions passed through a bicarbonate cartridge and lypholized to give the title compound as a white solid (9.9 mg, 10% yield).

$^1$H NMR (DMSO-d$_6$, 400 MHz): δ 1.02 (d, 6H), 1.35 (d, 3H), 1.36-1.56 (m, 4H), 1.57-1.70 (m, 3H), 1.79-1.88 (m, 1H), 2.20 (s, 3H), 2.40-2.43 (m, 4H), 3.04-3.06 (m, 4H), 3.09 (s, 3H), 3.24-3.29 (m, 2H), 4.78-4.99 (br m, 2H), 6.83 (d, 2H), 7.03 (br s, 1H), 7.16 (d, 2H), 7.73 (s, 1H).

MS (ES+) 492, (ES−) 490.

Example 26

(S)-9-cyclopentyl-2-(1-(4-((2-(dimethylamino)ethyl)(methyl)amino)phenyl)ethylamino)-5,7,7-trimethyl-8,9-dihydro-5H-pyrimido[4,5-b][1,4]diazepin-6(7H)-one Into an oven dried Schlenk tube dried under Argon was added (S)-2-(1-(4-bromophenyl)ethylamino)-9-cyclopentyl-5,7,7-trimethyl-8,9-dihydro-5H-pyrimido[4,5-b][1,4]diazepin-6(7H)-one (100 mg, 0.2096 mmol), CuI (1.996 mg, 0.01048 mmol), N,N-diethyl-2-hydroxy-benzamide (8.101 mg, 0.04192 mmol) and K$_3$PO$_4$ (88.98 mg, 0.4192 mmol). The tube was evacuated and re-filled with Argon (three times), and N,N',N'-trimethylethane-1,2-diamine (32.12 mg, 40.87 µL, 0.3144 mmol) in DMF (1 mL) was added and the reaction mixture was heated to 90° C. for 96 h. Additional CuI (1.996 mg, 0.01048 mmol), N,N-diethyl-2-hydroxy-benzamide (8.101 mg, 0.04192 mmol) and N,N',N'-trimethylethane-1,2-diamine (214.2 mg, 272.5 µL, 2.096 mmol) were added to the tube and the tube was re-charged with argon and heated to 90° C. overnight. The reaction mixture was then cooled to the ambient temperature and diluted with ethyl acetate (5 mL), water (5 mL) and ammonium hydroxide (0.2 mL). The aqueous layer was extracted with ethyl acetate (four times, 5 mL each), dried with MgSO$_4$, filtered and concentrated in vacuo. The crude product was purified by mass directed HPLC and product fractions combined and passed through a bicarbonate cartridge and lyophilized to give the title compound as a white solid (18.5 mg, 17% yield).

$^1$H NMR (DMSO-d$_6$, 400 MHz): δ 1.04 (d, 6H), 1.34 (d, 3H), 1.37-1.72 (m, 7H), 1.79-1.95 (m, 1H), 2.21 (s, 6H), 2.30-2.34 (m, 2H), 2.84 (s, 3H), 3.09 (s, 3H), 3.24-3.28 (m, 2H), 3.34-3.42 (m, 2H), 4.75 (br s, 1H), 5.04 (br s, 1H), 6.58 (d, 2H), 6.94 (br s, 1H), 7.13 (d, 2H), 7.73 (s, 1H).

MS (ES+) 494.

Example 12

PLK Assays

The compounds of the present invention are evaluated as inhibitors of human PLK kinase using the following assays.

PLK1 Inhibition Assay I:

Compounds were screened for their ability to inhibit PLK1 using a radioactive-phosphate incorporation assay. Assays were carried out in a mixture of 25 mM HEPES (pH 7.5), 10 mM MgCl$_2$, and 1 mM DTT. Final substrate concentrations were 350 µM [γ-33P]ATP (136 mCi 33P ATP/mmol ATP, Amersham Pharmacia Biotech/Sigma Chemicals) and 450 µM peptide (KKKISDELMDATFADQEAK) [SEQ. ID:1]. Assays were carried out at 25° C. in the presence of 2 nM PLK1. An assay stock buffer solution was prepared containing all of the reagents listed above, with the exception of ATP and the test compound of interest. 30 µL of the stock solution was placed in a 96 well plate followed by addition of 2 µL of DMSO stock containing serial dilutions of the test compound (typically starting from a final concentration of 10 µM with 2-fold serial dilutions) in duplicate (final DMSO concentration 5%). The plate was pre-incubated for 10 minutes at 25° C. and the reaction initiated by addition of 8 µL [γ-33P]ATP (final concentration 350 µM).

The reaction was stopped after 240 minutes by the addition of 100 µL 0.14M phosphoric acid. A multiscreen phosphocellulose filter 96-well plate (Millipore, Cat No. MAPHN0B50) was pretreated with 100 µL 0.1 M phosphoric acid prior to the addition of 125 µL of the stopped assay mixture. The plate was washed with 4×200 µL 0.1 M phosphoric acid. After drying, 100 µL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

PLK1 Inhibition Assay II:

Compounds were screened for their ability to inhibit PLK1 using a radioactive-phosphate incorporation assay. Assays were carried out in a mixture of 25 mM HEPES (pH 7.5), 10 mM $MgCl_2$, 0.1% BSA, and 2 mM DTT. Final substrate concentrations were 150 μM [γ-33P]ATP (115 mCi 33P ATP/mmol ATP, Amersham Pharmacia Biotech/Sigma Chemicals) and 300 μM peptide (KKKISDELMDATFADQEAK) [SEQ. ID:2]. Assays were carried out at 25° C. in the presence of 4 nM PLK1. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 150 μM).

The reaction was stopped after 90 minutes by the addition of 100 μL 0.14 M phosphoric acid. A multiscreen phosphocellulose filter 96-well plate (Millipore, Cat No. MAPHN0B50) was pretreated with 100 μL 0.1 M phosphoric acid prior to the addition of 125 μL of the stopped assay mixture. The plate was washed with 4×200 μL 0.1 M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

The compounds of this invention demonstrated inhibitory effect of different levels on PLK1. In some instances, the compounds of this invention demonstrated PLK1 inhibition at concentrations of less than 100 nM. In some other instances, the compounds of this invention demonstrated PLK1 inhibition at concentrations of between 1 nM and 10 nM.

PLK2 Inhibition Assay:

Compounds were screened for their ability to inhibit PLK2 using a radioactive-phosphate incorporation assay. Assays were carried out in a mixture of 25 mM HEPES (pH 7.5), 10 mM $MgCl_2$, 0.1% BSA, and 2 mM DTT. Final substrate concentrations were 200 μM [γ-33P]ATP (57 mCi 33P ATP/mmol ATP, Amersham Pharmacia Biotech/Sigma Chemicals) and 300 μM peptide (KKKISDELMDATFADQEAK) [SEQ ID:3]. Assays were carried out at 25° C. in the presence of 25 nM PLK2. An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 200 μM).

The reaction was stopped after 90 minutes by the addition of 100 μL 0.14 M phosphoric acid. A multiscreen phosphocellulose filter 96-well plate (Millipore, Cat No. MAPHN0B50) was pretreated with 100 μL 0.2M phosphoric acid prior to the addition of 125 μL of the stopped assay mixture. The plate was washed with 4×200 μl, 0.2 M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

PLK3 Inhibition Assay:

Compounds were screened for their ability to inhibit PLK3 using a radioactive-phosphate incorporation assay. Assays were carried out in a mixture of 25 mM HEPES (pH 7.5), 10 mM MgCl2, and 1 mM DTT. Final substrate concentrations were 75 μM [γ-33P]ATP (60 mCi 33P ATP/mmol ATP, Amersham Pharmacia Biotech/Sigma Chemicals) and 10 μM peptide (SAM68 protein A332-443). Assays were carried out at 25° C. in the presence of 5 nM PLK3 (S38-A340). An assay stock buffer solution was prepared containing all of the reagents listed above, with the exception of ATP and the test compound of interest. 30 μL of the stock solution was placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate was pre-incubated for 10 minutes at 25° C. and the reaction initiated by addition of 8 μL [γ-33P]ATP (final concentration 75 μM).

The reaction was stopped after 60 minutes by the addition of 100 μL 0.14 M phosphoric acid. A multiscreen phosphocellulose filter 96-well plate (Millipore, Cat No. MAPHN0B50) was pretreated with 100 μL 0.2M phosphoric acid prior to the addition of 125 μL of the stopped assay mixture. The plate was washed with 4×200 μL 0.2 M phosphoric acid. After drying, 100 μL Optiphase 'SuperMix' liquid scintillation cocktail (Perkin Elmer) was added to the well prior to scintillation counting (1450 Microbeta Liquid Scintillation Counter, Wallac).

After removing mean background values for all of the data points, Ki(app) data were calculated from non-linear regression analysis of the initial rate data using the Prism software package (GraphPad Prism version 3.0cx for Macintosh, GraphPad Software, San Diego Calif., USA).

PLK4 Inhibition Assay:

Compounds are screened for their ability to inhibit PLK4 using a radioactive-phosphate incorporation assay. Assays are carried out in a mixture of 8 mM MOPS (pH 7.5), 10 mM $MgCl_2$, 0.1% BSA and 2 mM DTT. Final substrate concentrations are 15 μM [γ-33P]ATP (227 mCi 33P ATP/mmol ATP, Amersham Pharmacia Biotech/Sigma Chemicals) and 300 μM peptide (KKKMDATFADQ) [SEQ ID:4]. Assays are carried out at 25° C. in the presence of 25 nM PLK4. An assay stock buffer solution is prepared containing all of the reagents listed above, with the exception of ATP and the test compound of interest. 30 μL of the stock solution is placed in a 96 well plate followed by addition of 2 μL of DMSO stock containing serial dilutions of the test compound (typically starting from a final concentration of 10 μM with 2-fold serial dilutions) in duplicate (final DMSO concentration 5%). The plate is pre-incubated for 10 minutes at 25° C. and the reaction initiated by addition of 8 μL [γ-33P]ATP (final concentration 15 μM).

The reaction is stopped after 180 minutes by the addition of 100 μL 0.14M phosphoric acid. A multiscreen phosphocellulose filter 96-well plate (Millipore, Cat No. MAPHN0B50) is pretreated with 100 μL 0.2 M phosphoric acid prior to the addition of 125 μL of the stopped assay mixture. The plate is washed with 4×200 μL 0.2 M phosphoric acid. After drying, 100 μL Optiphase 'SuperMix' liquid scintillation cocktail (Perkin Elmer) is added to the well prior to scintillation counting (1450 Microbeta Liquid Scintillation Counter, Wallac).

After removing mean background values for all of the data points, Ki(app) data are calculated from non-linear regression analysis of the initial rate data using the Prism software package (GraphPad Prism version 3.0cx for Macintosh, GraphPad Software, San Diego Calif., USA).

The compounds of this invention demonstrated inhibitory effect of different levels on PLK2, PLK3, or PLK4.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula I

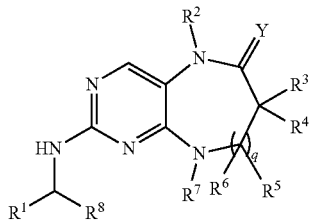

or a pharmaceutically acceptable salt thereof, wherein
Y is O or $NR^9$;
$R^1$ is aryl or 5-14 membered heteroaryl having 1-3 heteroatoms independently selected from N, O, or S, either of which is optionally substituted with 1-3 substituents independently selected from alkyl, halo, amino, alkoxy, haloalkyl, alkylsulfonyl, nitro, phenyl, piperazinyl, or alkylpiperazin-1-yl;
$R^2$ is H, alkyl, or cycloalkyl;
each of $R^3$ and $R^4$ is independently H, alkyl, cycloalkyl, aryl, or 5-14 membered heteroaryl having 1-3 heteroatoms independently selected from N, O, or S; or $R^3$ and $R^4$, together with the carbon atom to which they are attached, form a cycloalkyl;
each of $R^5$ and $R^6$ is independently H, alkyl, cycloalkyl, aryl, or 5-14 membered heteroaryl having 1-3 heteroatoms independently selected from N, O, or S;
$R^7$ is H, alkyl, cycloalkyl, aryl, 5-14 membered heteroaryl having 1-3 heteroatoms independently selected from N, O, or S, or 3-14 membered heterocyclyl having 1-3 heteroatoms independently selected from N, O, or S;
$R^8$ is alkyl optionally substituted with halo, —OH, or alkoxy;
$R^9$ is H or alkyl; or
$R^2$ and $R^9$, together with the atoms to which they are attached, form a 5- to 8-membered monocyclic ring containing additional 0 to 2 heteroatoms each independently selected from O, N, and S, wherein said monocyclic ring is optionally substituted with 0 to 4 groups each independently being alkyl, halo, alkoxy, or hydroxy; and
q is 0 or 1,
Provided that when q is 0, then Y is $NR^9$, and $R^2$ and $R^9$, together with the atoms to which they are attached, form a 5- to 8-membered monocyclic ring containing additional 0-2 hetero atoms each independently selected from O, N, and S, wherein said monocyclic ring is optionally substituted with 0 to 4 groups each independently being halo or alkyl.

2. The compound of claim 1, wherein $R^2$ is alkyl.
3. The compound of claim 2, wherein $R^2$ is methyl.
4. The compound of claim 1, wherein Y is O.
5. The compound of claim 1, wherein each of $R^3$ and $R^4$ is independently H or alkyl.
6. The compound of claim 5, wherein each of $R^3$ and $R^4$ is independently H, methyl, or ethyl.
7. The compound of claim 1, wherein $R^7$ is alkyl or cycloalkyl.
8. The compound of claim 7, wherein $R^7$ is cycloalkyl.
9. The compound of claim 8, wherein $R^7$ is cyclopentyl.
10. The compound claim 1, wherein each of $R^5$ and $R^6$ is independently H or alkyl.

11. The compound of claim 10, wherein each of $R^5$ and $R^6$ is H.
12. The compound of claim 1, wherein $R^8$ is methyl, ethyl, methoxymethyl, methoxyethyl, hydroxymethyl, or hydroxyethyl.
13. The compound of claim 12, wherein $R^8$ is methyl.
14. The compound of claim 13, wherein the carbon atom to which $R^8$ is attached is in the S configuration.
15. The compound of claim 1, wherein $R^1$ is phenyl, napthyl, pyridyl, furanyl or thiazolyl, each of which is optionally substituted with 1-3 substituents independently selected from alkyl, halo, amino, alkoxy, haloalkyl, alkylsulfonyl, nitro, phenyl, piperazinyl, or alkylpiperazin-1-yl.
16. The compound of claim 15, wherein $R^1$ is phenyl optionally substituted with 1 to 3 substituents each independently selected from the group consisting of alkyl, halo, amino, alkoxy, haloalkyl, alkylsulfonyl, nitro, phenyl, 1-piperazinyl, and 4-alkylpiperazin-1-yl.
17. The compound of claim 1, wherein $R^1$ is phenyl, 4-methylphenyl, 4-methoxyphenyl, 3-methoxyphenyl, 2-methoxyphenyl, 3,4-dimethoxyphenyl, 4-(trifluoromethoxy)phenyl, 2-(trifluoromethyl)phenyl, 4-(trifluoromethyl)phenyl, 3-(trifluoromethyl)phenyl, 3,5-bis(trifluoromethyl)phenyl, 4-bromophenyl, 4-chlorophenyl, 4-fluorophenyl, 2-fluorophenyl, 3,5-difluorophenyl, 4-(4-methylpiperazin-1-yl)phenyl, 4-(piperazin-1-yl)phenyl, 4-((2-(dimethylamino)ethyl)(methyl)amino)phenyl, 4-nitrophenyl, 4-(methylsulfonyl)phenyl, biphenyl-4-yl, naphthalenyl, 3-pyridinyl, 2-pyridinyl, 4-pyridinyl, 2-furanyl, 4-thiazolyl, or 2-methylthiazol-4-yl.
18. The compound of claim 1, wherein the compound is represented by Formula Ia

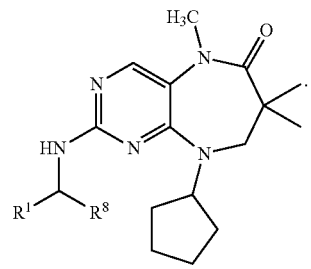

19. The compound of claim 1, wherein the compound is
9-cyclopentyl-5,7,7-trimethyl-2-(1-phenylethylamino)-8,9-dihydro-5H-pyrimido[4,5-b][1,4]diazepin-6(7H)-one;
9-cyclopentyl-5,7,7-trimethyl-2-(1-phenylpropylamino)-8,9-dihydro-5H-pyrimido[4,5-b][1,4]diazepin-6(7H)-one;
9-cyclopentyl-2-(2-methoxy-1-phenylethylamino)-5,7,7-trimethyl-8,9-dihydro-5H-pyrimido[4,5-b][1,4]diazepin-6(7H)-one;
9-cyclopentyl-2-(2-hydroxy-1-phenylethylamino)-5,7,7-trimethyl-8,9-dihydro-5H-pyrimido[4,5-b][1,4]diazepin-6(7H)-one;
2-(1-(4-bromophenyl)ethylamino)-9-cyclopentyl-5,7,7-trimethyl-8,9-dihydro-5H-pyrimido[4,5-b][1,4]diazepin-6(7H)-one;
9-cyclopentyl-5,7,7-trimethyl-2-(1-(4-(4-methylpiperazin-1-yl)phenyl)ethylamino)-8,9-dihydro-5H-pyrimido[4,5-b][1,4]diazepin-6(7H)-one;
9-cyclopentyl-5,7,7-trimethyl-2-(1-(4-(piperazin-1-yl)phenyl)ethylamino)-8,9-dihydro-5H-pyrimido[4,5-b][1,4]diazepin-6(7H)-one;

9-cyclopentyl-2-(1-(4-((2-(dimethylamino)ethyl)(methyl) amino)phenyl)ethylamino)-5,7,7-trimethyl-8,9-dihydro-5H-pyrimido[4,5-b][1,4]diazepin-6(7H)-one;

9-cyclopentyl-5,7,7-trimethyl-2-(1-p-tolylethylamino)-8, 9-dihydro-5H-pyrimido[4,5-b][1,4]diazepin-6(7H)-one;

2-(1-(4-chlorophenyl)ethylamino)-9-cyclopentyl-5,7,7-trimethyl-8,9-dihydro-5H-pyrimido[4,5-b][1,4]diazepin-6(7H)-one;

9-cyclopentyl-2-(1-(4-fluorophenyl)ethylamino)-5,7,7-trimethyl-8,9-dihydro-5H-pyrimido[4,5-b][1,4]diazepin-6(7H)-one;

9-cyclopentyl-2-(1-(2-fluorophenyl)ethylamino)-5,7,7-trimethyl-8,9-dihydro-5H-pyrimido[4,5-b][1,4]diazepin-6(7H)-one;

9-cyclopentyl-2-(1-(3,5-difluorophenyl)ethylamino)-5,7, 7-trimethyl-8,9-dihydro-5H-pyrimido[4,5-b][1,4]diazepin-6(7H)-one;

9-cyclopentyl-2-(1-(4-methoxyphenyl)ethylamino)-5,7, 7-trimethyl-8,9-dihydro-5H-pyrimido[4,5-b][1,4]diazepin-6(7H)-one;

9-cyclopentyl-2-(1-(3-methoxyphenyl)ethylamino)-5,7, 7-trimethyl-8,9-dihydro-5H-pyrimido[4,5-b][1,4]diazepin-6(7H)-one;

9-cyclopentyl-2-(1-(2-methoxyphenyl)ethylamino)-5,7, 7-trimethyl-8,9-dihydro-5H-pyrimido[4,5-b][1,4]diazepin-6(7H)-one;

9-cyclopentyl-2-(1-(3,4-dimethoxyphenyl)ethylamino)-5, 7,7-trimethyl-8,9-dihydro-5H-pyrimido[4,5-b][1,4]diazepin-6(7H)-one;

9-cyclopentyl-5,7,7-trimethyl-2-(1-(4-(trifluoromethoxy) phenyl)ethylamino)-8,9-dihydro-5H-pyrimido[4,5-b] [1,4]diazepin-6(7H)-one;

9-cyclopentyl-5,7,7-trimethyl-2-(1-(4-(trifluoromethyl) phenyl)ethylamino)-8,9-dihydro-5H-pyrimido[4,5-b] [1,4]diazepin-6(7H)-one;

9-cyclopentyl-5,7,7-trimethyl-2-(1-(3-(trifluoromethyl) phenyl)ethylamino)-8,9-dihydro-5H-pyrimido[4,5-b] [1,4]diazepin-6(7H)-one;

2-(1-(3,5-bis(trifluoromethyl)phenyl)ethylamino)-9-cyclopentyl-5,7,7-trimethyl-8,9-dihydro-5H-pyrimido[4, 5-b][1,4]diazepin-6(7H)-one;

9-cyclopentyl-5,7,7-trimethyl-2-(1-(2-(trifluoromethyl) phenyl)ethylamino)-8,9-dihydro-5H-pyrimido[4,5-b] [1,4]diazepin-6(7H)-one;

9-cyclopentyl-5,7,7-trimethyl-2-(1-(4-nitrophenyl)ethylamino)-8,9-dihydro-5H-pyrimido[4,5-b][1,4]diazepin-6(7H)-one;

9-cyclopentyl-5,7,7-trimethyl-2-(1-(4-(methylsulfonyl) phenyl)ethylamino)-8,9-dihydro-5H-pyrimido[4,5-b] [1,4]diazepin-6(7H)-one;

2-(1-(biphenyl-4-yl)ethylamino)-9-cyclopentyl-5,7,7-trimethyl-8,9-dihydro-5H-pyrimido[4,5-b][1,4]diazepin-6(7H)-one;

9-cyclopentyl-5,7,7-trimethyl-2-(1-(naphthalen-1-yl) ethylamino)-8,9-dihydro-5H-pyrimido[4,5-b][1,4]diazepin-6(7H)-one;

9-cyclopentyl-5,7,7-trimethyl-2-(1-(pyridin-3-yl)ethylamino)-8,9-dihydro-5H-pyrimido[4,5-b][1,4]diazepin-6(7H)-one;

9-cyclopentyl-5,7,7-trimethyl-2-(1-(pyridin-2-yl)ethylamino)-8,9-dihydro-5H-pyrimido[4,5-b][1,4]diazepin-6(7H)-one;

9-cyclopentyl-5,7,7-trimethyl-2-(1-(pyridin-4-yl)ethylamino)-8,9-dihydro-5H-pyrimido[4,5-b][1,4]diazepin-6(7H)-one;

9-cyclopentyl-2-(1-(furan-2-yl)ethylamino)-5,7,7-trimethyl-8,9-dihydro-5H-pyrimido[4,5-b][1,4]diazepin-6 (7H)-one; or 9-cyclopentyl-5,7,7-trimethyl-2-(1-(2-methylthiazol-4-yl)ethylamino)-8,9-dihydro-5H-pyrimido[4,5-b][1,4] diazepin-6(7H)-one.

20. The compound of claim 1, wherein the carbon atom to which $R^3$ and $R^4$ are attached is in the R configuration.

21. The compound of claim 1, wherein Y is $NR^9$.

22. The compound of claim 21, wherein $R^2$ and $R^9$, together with the atoms to which they are attached, form a 5- to 8-membered monocyclic ring containing additional 0-2 hetero atoms each independently selected from O, N, and S, wherein said monocyclic ring is optionally substituted with 0 to 4 groups each independently being halo or alkyl.

23. The compound of claim 21, wherein each of $R^3$ and $R^4$ is independently H or alkyl.

24. The compound of claim 23, wherein $R^3$ is ethyl and $R^4$ is H.

25. The compound of claim 21, wherein $R^7$ is cycloalkyl.

26. The compound of claim 25, wherein $R^7$ is cyclopentyl.

27. The compound of claim 21, wherein $R^7$ is aryl.

28. The compound of claim 27, wherein $R^7$ is phenyl.

29. The compound of claim 21, wherein $R^1$ is aryl optionally substituted with 1-3 substituents independently selected from alkyl, halo, amino, alkoxy, haloalkyl, alkylsulfonyl, nitro, phenyl, piperazinyl, or alkylpiperazin-1-yl.

30. The compound of claim 29, wherein $R^1$ is phenyl, p-bromophenyl, or 4-methylpiperazin-1-yl.

31. The compound of claim 21, wherein $R^8$ is alkyl optionally substituted with halo, —OH, or alkoxy.

32. The compound of claim 31, wherein $R^8$ is methyl, ethyl, methoxymethyl, methoxyethyl, hydroxymethyl, or hydroxyethyl.

33. The compound of claim 32, wherein $R^8$ is methyl.

34. The compound of claim 33, wherein the carbon to which $R^8$ is attached is in the S configuration.

35. The compound of claim 1, wherein the compound is:

(S)-9-cyclopentyl-5,7,7-trimethyl-2-(1-phenylethylamino)-8,9-dihydro-5H-pyrimido[4,5-b][1,4]diazepin-6(7H)-one;

(S)-9-cyclopentyl-5,7,7-trimethyl-2-(1-phenylpropylamino)-8,9-dihydro-5H-pyrimido[4,5-b][1,4]diazepin-6(7H)-one;

(R)-9-cyclopentyl-2-(2-methoxy-1-phenylethylamino)-5, 7,7-trimethyl-8,9-dihydro-5H-pyrimido[4,5-b][1,4]diazepin-6(7H)-one;

(R)-9-cyclopentyl-2-(2-hydroxy-1-phenylethylamino)-5, 7,7-trimethyl-8,9-dihydro-5H-pyrimido[4,5-b][1,4]diazepin-6(7H)-one;

(S)-2-(1-(4-bromophenyl)ethylamino)-9-cyclopentyl-5,7, 7-trimethyl-8,9-dihydro-5H-pyrimido[4,5-b][1,4]diazepin-6(7H)-one;

(S)-9-cyclopentyl-5,7,7-trimethyl-2-(1-(4-(4-methylpiperazin-1-yl)phenyl)ethylamino)-8,9-dihydro-5H-pyrimido[4,5-b][1,4]diazePin-6(7H)-one;

(S)-9-cyclopentyl-5,7,7-trimethyl-2-(1-p-tolylethylamino)-8,9-dihydro-5H-pyrimido[4,5-b][1,4]diazepin-6(7H)-one;

(S)-2-(1-(4-chlorophenyl)ethylamino)-9-cyclopentyl-5,7, 7-trimethyl-8,9-dihydro-5H-pyrimido[4,5-b][1,4]diazepin-6(7H)-one;

(S)-9-cyclopentyl-2-(1-(4-fluorophenyl)ethylamino)-5,7, 7-trimethyl-8,9-dihydro-5H-pyrimido[4,5-b][1,4]diazepin-6(7H)-one;

(S)-9-cyclopentyl-2-(1-(4-methoxyphenyl)ethylamino)-5,7,7-trimethyl-8,9-dihydro-5H-pyrimido[4,5-b][1,4]diazepin-6(7H)-one;

(S)-9-cyclopentyl-2-(1-(3-methoxyphenyl)ethylamino)-5,7,7-trimethyl-8,9-dihydro-5H-pyrimido[4,5-b][1,4]diazepin-6(7H)-one;

(S)-9-cyclopentyl-2-(1-(2-methoxyphenyl)ethylamino)-5,7,7-trimethyl-8,9-dihydro-5H-pyrimido[4,5-b][1,4]diazepin-6(7H)-one;

(S)-9-cyclopentyl-5,7,7-trimethyl-2-(1-(2-(trifluoromethyl)phenyl)ethylamino)-8,9-dihydro-5H-pyrimido[4,5-b][1,4]diazepin-6(7H)-one;

(S)-9-cyclopentyl-5,7,7-trimethyl-2-(1-(4-nitrophenyl)ethylamino)-8,9-dihydro-5H-pyrimido[4,5-b][1,4]diazepin-6(7H)-one;

(R,S)-9-cyclopentyl-5,7,7-trimethyl-2-(1-(4-(methylsulfonyl)phenyl)ethylamino)-8,9-dihydro-5H-pyrimido[4,5-b][1,4]diazepin-6(7H)-one;

(R,S)-2-(1-(biphenyl-4-yl)ethylamino)-9-cyclopentyl-5,7,7-trimethyl-8,9-dihydro-5H-pyrimido[4,5-b][1,4]diazepin-6(7H)-one;

(R,S)-9-cyclopentyl-5,7,7-trimethyl-2-(1-(naphthalen-1-yl)ethylamino)-8,9-dihydro-5H-pyrimido[4,5-b][1,4]diazepin-6(7H)-one;

(R,S)-9-cyclopentyl-5,7,7-trimethyl-2-(1-(pyridin-3-yl)ethylamino)-8,9-dihydro-5H-pyrimido[4,5-b][1,4]diazepin-6(7H)-one;

(R,S)-9-cyclopentyl-5,7,7-trimethyl-2-(1-(pyridin-4-yl)ethylamino)-8,9-dihydro-5H-pyrimido[4,5-b][1,4]diazepin-6(7H)-one;

(R,S)-9-cyclopentyl-2-(1-(furan-2-yl)ethylamino)-5,7,7-trimethyl-8,9-dihydro-5H-pyrimido[4,5-b][1,4]diazepin-6(7H)-one;

(R,S)-9-cyclopentyl-2-(1-(3,4-dimethoxyphenyl)ethylamino)-5,7,7-trimethyl-8,9-dihydro-5H-pyrimido[4,5-b][1,4]diazepin-6(7H)-one;

(R,S)-9-cyclopentyl-5,7,7-trimethyl-2-(1-(4-(trifluoromethoxy)phenyl)ethylamino)-8,9-dihydro-5H-pyrimido[4,5-b][1,4]diazepin-6(7H)-one;

(R)—N—((S)-1-(4-bromophenyl)ethyl)-5-cyclopentyl-4-ethyl-4,5-dihydro-[1,2,4]triazolo[4,3-f]pteridin-7-amine;

(R)-5-cyclopentyl-4-ethyl-N—((S)-1-phenylethyl)-4,5-dihydro-[1,2,4]triazolo[4,3-f]pteridin-7-amine;

(S)-9-cyclopentyl-2-(1-(4-((2-(dimethylamino)ethyl)(methyl)amino)phenyl)ethylamino)-5,7,7-trimethyl-8,9-dihydro-5H-pyrimido[4,5-b][1,4]diazepin-6(7H)-one;

(R,S)-9-cyclopentyl-5,7,7-trimethyl-2-(1-(2-methylthiazol-4-yl)ethylamino)-8,9-dihydro-5H-pyrimido[4,5-b][1,4]diazepin-6(7H)-one;

(S)-9-cyclopentyl-5,7,7-trimethyl-2-(1-(3-(trifluoromethyl)phenyl)ethylamino)-8,9-dihydro-5H-pyrimido[4,5-b][1,4]diazepin-6(7H)-one;

(R,S)-9-cyclopentyl-2-(1-(2-fluorophenyl)ethylamino)-5,7,7-trimethyl-8,9-dihydro-5H-pyrimido[4,5-b][1,4]diazepin-6(7H)-one;

(R,S)-9-cyclopentyl-2-(1-(3,5-difluorophenyl)ethylamino)-5,7,7-trimethyl-8,9-dihydro-5H-pyrimido[4,5-b][1,4]diazepin-6(7H)-one;

(S)-9-cyclopentyl-5,7,7-trimethyl-2-(1-(4-(trifluoromethyl)phenyl)ethylamino)-8,9-dihydro-5H-pyrimido[4,5-b][1,4]diazepin-6(7H)-one;

(S)-2-(1-(3,5-bis(trifluoromethyl)phenyl)ethylamino)-9-cyclopentyl-5,7,7-trimethyl-8,9-dihydro-5H-pyrimido[4,5-b][1,4]diazepin-6(7H)-one (R)-4-ethyl-5-phenyl-N—((S)-1-phenylethyl)-4,5-dihydro-[1,2,4]triazolo[4,3-f]pteridin-7-amine;

(R)—N—((S)-1-(4-bromophenyl)ethyl)-5-cyclopentyl-4-ethyl-4,5-dihydro-[1,2,4]triazolo[4,3-f]pteridin-7-amine;

(R)-5-cyclopentyl-4-ethyl-N—((S)-1-(4-(4-methylpiperazin-1-yl)phenyl)ethyl)-4,5-dihydro-[1,2,4]triazolo[4,3-f]pteridin-7-amine; or (R)-5-cyclopentyl-4-ethyl-N—((S)-1-(4-(piperazin-1-yl)phenyl)ethyl)-4,5-dihydro-[1,2,4]triazolo[4,3-f]pteridin-7-amine.

36. A composition comprising a compound of claim 1, and a pharmaceutically acceptable carrier, adjuvant, or vehicle.

\* \* \* \* \*